(12) United States Patent
Rudolph et al.

(10) Patent No.: US 8,268,293 B2
(45) Date of Patent: Sep. 18, 2012

(54) UV PROTECTION

(75) Inventors: Thomas Rudolph, Darmstadt (DE); Herwig Buchholz, Frankfurt (DE)

(73) Assignee: Merck Patent GmbH, Darmstadt (DE)

( * ) Notice: Subject to any disclaimer, the term of this patent is extended or adjusted under 35 U.S.C. 154(b) by 1331 days.

(21) Appl. No.: 11/911,888

(22) PCT Filed: Mar. 21, 2006

(86) PCT No.: PCT/EP2006/002593
§ 371 (c)(1),
(2), (4) Date: Oct. 18, 2007

(87) PCT Pub. No.: WO2006/111234
PCT Pub. Date: Oct. 26, 2006

(65) Prior Publication Data
US 2008/0171004 A1 Jul. 17, 2008

(30) Foreign Application Priority Data

Apr. 19, 2005 (DE) .......................... 10 2005 018 184
Nov. 28, 2005 (EP) ..................... 05025917

(51) Int. Cl.
*A61K 8/00* (2006.01)
*A61K 8/18* (2006.01)
*A61Q 17/04* (2006.01)

(52) U.S. Cl. ....................................................... 424/59
(58) Field of Classification Search ........................ None
See application file for complete search history.

(56) References Cited

U.S. PATENT DOCUMENTS

| | | | |
|---|---|---|---|
| 2,415,624 A * | 2/1947 | Brown et al. ................ | 430/512 |
| 4,069,340 A | 1/1978 | Pattison | |
| 5,175,340 A | 12/1992 | Forestier et al. | |
| 5,453,514 A | 9/1995 | Niigata et al. | |
| 2003/0049214 A1 * | 3/2003 | Muller ........................... | 424/59 |

FOREIGN PATENT DOCUMENTS

| | | |
|---|---|---|
| DE | 20 35 334 A1 | 2/1971 |
| DE | 101 24 914 A1 | 11/2002 |
| EP | 0054 174 A | 6/1982 |
| EP | 0511666 A | 6/1982 |
| EP | 0100651 A | 2/1984 |
| EP | 1266888 A | 12/2002 |
| EP | 1604643 A | 12/2005 |
| JP | 01 013017 A | 1/1989 |
| WO | WO 00/58260 A1 | 10/2000 |
| WO | WO 02/094209 A | 11/2002 |
| WO | WO 02094209 A2 * | 11/2002 |
| WO | WO 03/007906 A | 1/2003 |

OTHER PUBLICATIONS

Nadim A. Shaath, "Ultraviolet filters" Photochemical & Photobiological Sciences, Feb. 2010, vol. 9, pp. 464-469.*
Giacomoni et al., "Sunscreens: impervious path from theory to practice" Photochemical & Photobiological Sciences, 2010, vol. 9, pp. 524-529.*
STN structure and CAS registry number results for WO 02/094209 A2, obtained from STN CAPLUS database Jun. 21, 2011.*
Irie, H. et al: "New Synthesis of Isoquinoline Alkaloids, Thalifoline, Corypalline, and Cherylline" Chemistry Letters, Chemical Society of Japan. Tokyo, JP, NR. 7, (Jul. 1, 1980), Seiten 875-878, XP000567042.
Chuang, C-P et al: "Manganese (III) Acetate Initiated Oxidative Free Radical Reaction Between 1,4-Naphthoquinones and Alpha-Alkylmalonates" Tetrahedron, Elsevier Science Publishers, Amsterdam, NL, BD. 54, NR. 34, (Aug. 20, 1998), Seiten 10043-10052, XP004129982.
Russell, P.B.; Hitchings, G.H.: "Some 2,4,6-Triamino-5-Alkyl-and 5-Benzylpyrimidines" J. Am. Chem. Soc., BD. 74, NR. 13, 1952, Seiten 3443-3444, XP002393650.
Diana, G.D., et al: "Antiviral Activity of Some Beta-Diketones. 4. Benzyl Diketones. In Vitro Activity Against Both RNA and DNA Viruses" J. Med. Chem., BD. 21, NR. 9, 1978, Seiten 322-325, XP009070577.
Kujundzic, N. et al.: "Synthesis and Antibacterial Effect of Derivatives of 5-(3,4,5-Trimethoxybenzyl)-Pyrimidine, -Tetrahydropyrimidine, - Hexahydropyrimidine and -Hydantoin" Croatica Chemica Acta,BD. 61, NR. 1, 1988, Seiten 121-135, XP009070565.
Jew, Sang-Sup et al: "Enantioselective Synthesis of Eucomols Using Sharpless Catalytic Asymmetric Dihydroxylation" Heterocycles, BD. 46, 1997, Seiten 65-70, XP00907501.
Kirkiacharian, B. Serge et al: "Hydride Reduction of Coumarin Derivatives:New Method of Synthsis of 2'-Hydroxybenzylmalonic Esters" Comptes Rendus Des Seances De L'Academie Des Sciences, Serie 2: Mecanique-Physique, Chimie, Sciences De L'Univers, Sciences De La Terre, BD. 294, NR. 3, 1982, Seiten 181-184, XP009070516.
Sohda, T. et al: "Antiulcer Activity of 5-Benzylthiazolidine-2, 4-Dione Derivatives" Chemical and Pharmaceutical Bulletin, Pharmaceutical Society of Japan, Tokyo, JP, BD. 31, NR. 2, (Feb. 1983), Seiten 560-569, XP002193484.
Chraibi, A. et al: "Pyrazolidine-Diones. I. Synthese De Dihydrazides Benzylmaloniques Et Arylcyclopropaniques" Annales Pharmaceutiques Francaises, BD. 38, NR. 4M 1980, Seiten 343-352, XP009070510.
Hey, D.H.; Nagdy, K.A.: "Intermolecular Acylation. III. The Preparation and Ring Closure of the .Alpha.-(Methoxyphenyl) Glutaric Acids" J. on Chem. Soc., 1953, Seiten 1894-1899, XP009007023.
Bey.P,: Schirlin.D.: "General Approach to the Synthesis of Alpha-Difluoromethyl Amines as Potential Enzyme-Activated Irreversible Inhibitors" Tetrahedron Letters, BD. 19, NR. 52, 1978, Seiten 5225, 5228, XP002393651.
Westfahl, J. C.; Gresham. T.L.: "Vinylidene Cyanide. V. The Aluminum Chloride Catalyzed Reaction of Vinylidene Cyanide and Aromatic Compounds" J. Am. Chem. Soc., BD. 76, NR. 4, 1954, Seiten 1076-1080, XP002393652.
Dean. F.M., et al.: "The Chemistry of Fungi. Part IX. 3,4Dihydrocoumarins" J. Chem. Soc., 1950, Seiten 895-902, XP009070552.
J. Olea Science (2002), 51 (1), 57-62, M. Nomura et al.
Cook, J.W. et al.: "86. Colchicine and Related Compounds. Part III" J. Chem. Soc., 1944, Seiten 322-325, XP009070577.

* cited by examiner

*Primary Examiner* — Johann Richter
*Assistant Examiner* — Daniel L Branson
(74) *Attorney, Agent, or Firm* — Millen, White, Zelano, Branigan, P.C.

(57) ABSTRACT

The present invention relates to the use of compounds which do not themselves exhibit significant UV absorption in the UV-A or UV-B region, but are reactive under use conditions, for the development of UV-A or UV-B protection during use, to corresponding novel compounds and compositions, and to corresponding processes for the preparation of compounds and compositions.

15 Claims, 3 Drawing Sheets

UV PROTECTION

Figure 1A:
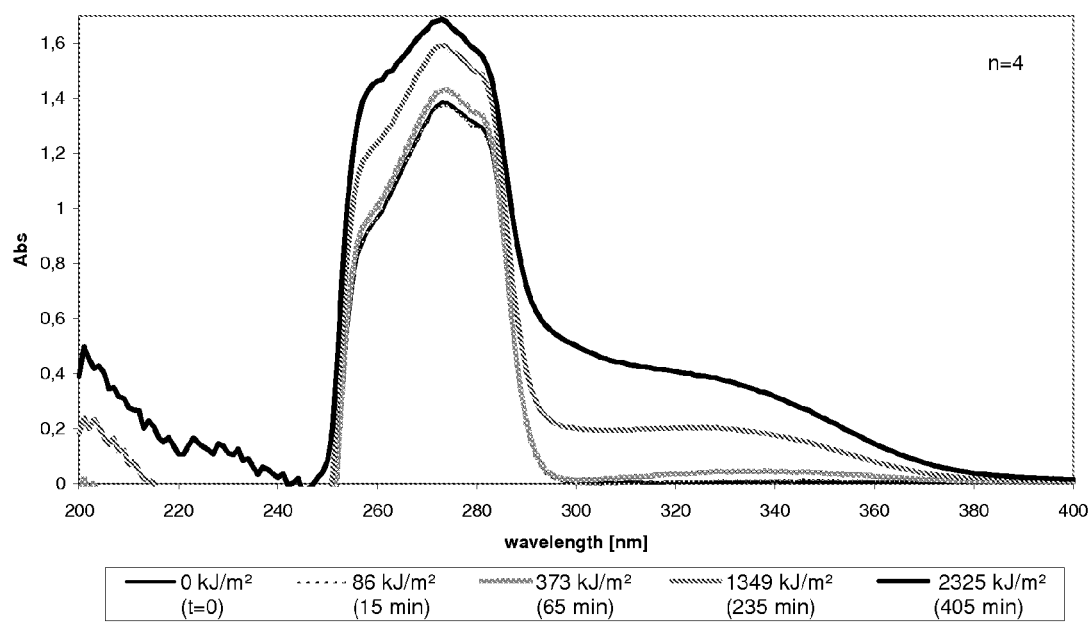

The present invention relates to the use of compounds which do not themselves exhibit significant UV absorption in the UV-A or UV-B region, but are reactive under use conditions, for the development of UV-A or UV-B protection during use, to corresponding novel compounds and compositions, and to corresponding processes for the preparation of compounds and compositions.

One area of application of the compounds according to the invention is, for example, cosmetics. The object of care cosmetics is wherever possible to obtain the impression of youthful skin. In principle, there are various ways of achieving this object. For example, existing skin damage, such as irregular pigmentation or the formation of wrinkles, can be compensated for by covering powders or creams. Another approach is to protect the skin against environmental influences which lead to permanent damage and thus ageing of the skin. The idea is therefore to intervene in a preventative manner and thus to delay the ageing process. An example of this are UV filters, which, as a result of absorption of certain wavelength ranges, prevent or at least reduce skin damage. Whereas in the case of UV filters the damaging event, the UV radiation, is screened off by the skin, another route involves attempting to support the skin's natural defence or repair mechanisms against the damaging event. Finally, a further approach involves compensating for the weakening defence functions of the skin against harmful influences with increasing age by externally supplying substances which are able to replace this diminishing defence or repair function. For example, the skin has the ability to scavenge free radicals generated by external or internal stress factors. This ability diminishes with increasing age, causing the ageing process to accelerate with increasing age.

A certain degree of tanning of the skin is regarded in modern society as attractive and as an expression of vigour and sportiness. In addition to this desired action of the sun on the skin, a number of undesired side effects occur, such as sunburn or premature skin ageing and wrinkling. Of particular importance here is the wavelength range from 280 to 400 nm. This range covers UV-B rays having a wavelength of between 280 and 320 nm, which play a crucial role in the formation of solar erythema, and also UV-A rays having a wavelength of between 320 and 400 nm, which tan the skin, but also allow ageing, favour the triggering of an erythematous reaction or can exacerbate this reaction in certain people or even trigger phototoxic or photoallergic and irritative reactions.

Skin damage is not caused just by sunlight, but also by other external influences, such as cold or heat. Furthermore, the skin undergoes natural ageing, with the formation of wrinkles and a reduction in the elasticity of the skin.

A further difficulty in the preparation of cosmetics is that active ingredients which are intended to be incorporated into cosmetic compositions are frequently unstable and can be damaged in the composition. The damage may be caused, for example, by a reaction with atmospheric oxygen or by absorption of UV rays. The molecules damaged in this way may, for example, change their colour and/or lose their activity through their structural change.

This applies in particular to conventional UV filters. Recently, however, so-called photostable UV filters, such as, for example, Uvinul® A Plus from BASF, which are substantially stable on storage are increasingly coming onto the market.

In addition, a trend is evident to provide not only typical sunscreens, but also day-care products, with UV protection. The background is the above-described promotion of skin ageing by UV radiation.

However, it is necessary, inter alia, for vitamin D synthesis in the skin for a certain amount of UV radiation to hit the skin. This is not always guaranteed in times of low UV intensity, such as, for example, in winter. The above-described care products with UV protection further reduce the UV dose which reaches the skin.

It would therefore be desirable if—in particular for day-care products—UV protection could be provided which allows low UV doses to pass through, but reduces their harmful effect and activates itself at higher radiation doses.

The object of the invention is therefore to provide a composition which has a protective action against UV rays when needed and/or exerts a protective action against oxidative stress on body cells and/or counters premature ageing of the skin.

The present invention therefore relates firstly to the use of compounds which do not themselves exhibit significant UV absorption in the UV-A or UV-B region, but are reactive under use conditions, for the development of UV-A or UV-B protection during use.

It has been found that the production of UV protection can take place here by various mechanisms. Thus, preferred compounds react with reactive species, such as, in particular, free radicals, under use conditions and thus form products which offer UV-A or UV-B protection. A further class of compounds preferably to be employed in accordance with the invention is reacted under use conditions of skin enzymes and thus forms products which offer UV-A or UV-B protection. A further class of compounds preferably to be employed in accordance with the invention is decomposed under use conditions due to supply of heat and thus forms products which offer UV-A or UV-B protection.

Particular preference is given in accordance with the invention to the use of compounds of the formula I

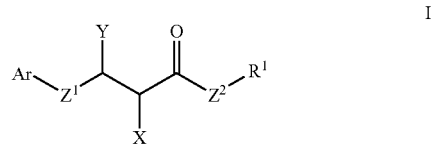

where

Ar stands for an unsubstituted or mono- or polysubstituted aromatic ring or condensed ring systems having 6 to 18 C atoms, at least one ring of which has an aromatic character and in which one or two CH groups per ring may be replaced by C=O, N, O or S and, in addition, one or two $CH_2$ groups in a condensed ring system may be replaced by C=O or C=$CH_2$, $R^1$ stands for H or a branched or unbranched $C_{1-30}$-alkyl or $C_{1-30}$-hydroxyalkyl radical or a radical $R^a$ or $R^b$

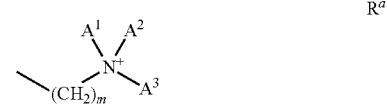

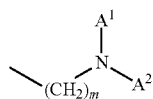

where m stands for an integer from the range from 1 to 30, and $A^1$-$A^3$ each, independently of one another, stand for a benzyl radical or a —$(CH_2O)_n(CH_2)_o(O)_pH$ radical, where m and o each, independently of one another, stand for an integer from the range from 0 to 30, and p stands for 0 or 1, X stands for a group selected from —H, —CN, —C(=O)—$R^1$ and —C(=O)—$Z^2$—$R^1$, Y stands for H or Ar, $Z^1$ and $Z^2$ each, independently of one another, stand for O, S, $CR^7R^8$, $NR^7$ or a single bond, $R^7$ and $R^8$ are each, independently of one another, selected from H, OH, straight-chain or branched $C_1$- to $C_{20}$-alkoxy groups, straight-chain or branched $C_1$- to $C_{20}$-alkyl groups, straight-chain or branched $C_3$- to $C_{20}$-alkenyl groups, straight-chain or branched $C_1$- to $C_{20}$-hydroxyalkyl groups, where the hydroxyl group may be bonded to a primary or secondary carbon atom of the chain and furthermore the alkyl chain may also be interrupted by oxygen, straight-chain or branched $C_1$- to $C_{20}$-hydroxyalkoxy groups, where the hydroxyl group(s) may be bonded to a primary or secondary carbon atom of the chain and furthermore the alkyl chain may also be interrupted by oxygen, salts of the compounds of the formula I.

Preference is given in accordance with the invention to the use of compounds of the formula Ia

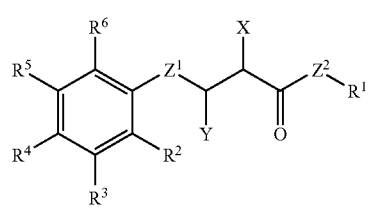

where $R^1$, $R^7$ and $R^8$, $Z^1$ and $Z^2$, X and Y have the meaning given in claim 5, $R^2$ to $R^6$ are each, independently of one another, selected from H, OH, straight-chain or branched $C_1$- to $C_{20}$-alkoxy groups, straight-chain or branched $C_1$- to $C_{20}$-alkyl groups, straight-chain or branched $C_3$- to $C_{20}$-alkenyl groups, straight-chain or branched $C_1$- to $C_{20}$-hydroxyalkyl groups, where the hydroxyl group may be bonded to a primary or secondary carbon atom of the chain and furthermore the alkyl chain may also be interrupted by oxygen, straight-chain or branched $C_1$- to $C_{20}$-hydroxyalkoxy groups, where the hydroxyl group(s) may be bonded to a primary or secondary carbon atom of the chain and furthermore the alkyl chain may also be interrupted by oxygen, where one of the radicals $R^2$ to $R^6$ may also stand for a branched or unbranched $C_{1-20}$-alkoxy or branched or unbranched $C_{2-20}$-alkyleneoxy spacer which is bonded to an oligo- or polysiloxane chain via an Si atom, or salts of the compounds of the formula Ia.

In a particularly preferred embodiment of the present invention, $Z^1$ in the compound of the formula Ia stands for a single bond. In this case, the formula Ia is simplified to

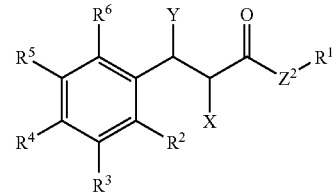

It may furthermore be particularly preferred in accordance with the invention for

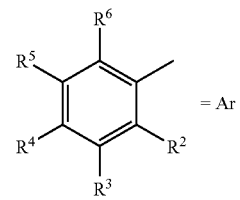

Counterions which can be employed here for salts according to the invention are all anions which are acceptable for the corresponding application. Salts of strong acids are advantageous here. It is particularly preferred in accordance with the invention for the salts to be chlorides or bromides.

The compounds described can be used in accordance with the invention as active ingredient for topical application or for the preparation of cosmetic or dermatological compositions or for the preparation of domestic products. The compounds described can be employed for product protection. For the purposes of this application, product protection means, in particular, the protection of oxidation-sensitive formulation constituents, such as organic or inorganic dyes, antioxidants, vitamins, perfume components, oil components or matrix constituents, such as emulsifiers, thickeners, film formers and surfactants.

The invention particularly preferably relates to the use of at least one compound of the formula I or Ia as UV filter precursor which can be activated by UV radiation and/or reactive oxygen species, such as, for example, oxygen free radicals. The invention also relates to the use of the compounds for the preparation of cosmetic or dermatological compositions or of foods or food supplements or for the preparation of domestic products.

The present invention furthermore relates to the novel compounds of the formula I or Ia.

Preference is given here to the use of compounds of the formula I or Ia in which $R^3$ and $R^5$ are each, independently of one another, selected from H, straight-chain or branched $C_1$- to $C_{20}$-alkoxy groups, straight-chain or branched $C_1$- to $C_{20}$-alkyl groups, straight-chain or branched $C_3$- to $C_{20}$-alkenyl groups, straight-chain or branched $C_1$- to $C_{20}$-hydroxyalkyl groups, where the hydroxyl group may be bonded to a primary or secondary carbon atom of the chain and furthermore the alkyl chain may also be interrupted by oxygen, straight-chain or branched $C_1$- to $C_{20}$-hydroxyalkoxy groups, where the hydroxyl group(s) may be bonded to a primary or secondary carbon atom of the chain and furthermore the alkyl chain may also be interrupted by oxygen, where $R^3$ and $R^5$ are each, independently of one another, preferably selected from straight-chain or branched $C_1$- to $C_4$alkoxy groups, in particular methoxy, isopropoxy and tert-butoxy, and straight-chain or branched $C_1$- to $C_6$-alkyl groups, in particular methyl, isopropyl and tert-butyl, and $R^2$, $R^4$ and $R^6$ are each, independently of one another, selected from H, OH, straight-chain or branched $C_1$- to $C_{20}$-alkoxy groups, straight-chain or branched $C_1$- to $C_{20}$-alkyl groups, straight-chain or branched $C_3$- to $C_{20}$-alkenyl groups, straight-chain or branched $C_1$- to $C_{20}$-hydroxyalkyl groups, where the hydroxyl group may be bonded to a primary or secondary carbon atom of the chain and furthermore the alkyl chain may also be interrupted by oxygen, straight-chain or branched $C_1$- to $C_{20}$-hydroxyalkoxy groups, where the hydroxyl group(s) may be bonded to a primary or secondary carbon atom of the chain and furthermore the alkyl chain may also be interrupted by oxygen, where $R^2$, $R^4$ and $R^6$ are preferably selected from H and OH, and where one of the radicals $R^2$ to $R^6$ may also stand for a branched or unbranched $C_{1-20}$-alkoxy or branched or unbranched $C_{2-20}$-alkyleneoxy spacer which is bonded via an Si atom to an oligo- or polysiloxane chain, which in turn contains one or more compounds of the formula I.

In a variant of the invention, particular preference may be given to the use of at least one compound of the formula I which is characterised in that at least one group from $R^2$, $R^4$ and $R^6$ stands for OH. These compounds exhibit a particularly pronounced antioxidative performance.

In a further variant of the invention, particular preference may be given to the use of at least one compound of the formula I which is characterised in that at least one group from $R^3$ and $R^5$ stands for t-butyl. These compounds exhibit a particularly pronounced antioxidative performance.

Preference may furthermore be given in accordance with the invention to the use of at least one compound of the formula I or Ia containing long-chain hydrocarbon radicals, in particular branched long-chain hydrocarbon radicals. These compounds are often particularly readily miscible with vehicles, such as, in particular, oils, and can thus be employed particularly easily in formulations. It is particularly preferred in this variant of the invention for $R^1$ to stand for a branched or unbranched $C_{7-30}$-alkyl or $C_{6-30}$-hydroxyalkyl radical.

In a further variant of the invention, it may be preferred to use compounds of the formula I or Ia which are characterised in that $R^4$ stands for a branched or unbranched $C_{1-20}$-alkoxy or branched or unbranched $C_{2-20}$-alkyleneoxy spacer which is bonded via an Si atom to an oligo- or polysiloxane chain which contains one or more compounds of the formula I, where $R^4$ preferably stands for a propanyloxy, isopropanyloxy, propenyloxy, isopropenyloxy or in particular an allyloxy spacer, where a silicon atom is preferably bonded to the 1-C or 2-C of the spacer double bond.

It may furthermore be preferred in accordance with the invention to use at least one compound of the formula I in which X stands for —C(=O)—$Z^2$—$R^1$, where the two radicals —$Z^2$—$R^1$ are identical, and $R^2$ to $R^6$ each, independently of one another, preferably stand for H, hydroxyl or methoxy.

Particular preference is given here to the use of at least one compound of the formula I which is selected from 4-hydroxyphenylpropionic acid, 2-ethylhexyl 4-hydroxyphenylpropionate, di-2-ethylhexyl 4-hydroxy-3,5-dimethoxybenzylmalonate, di-2-ethylhexyl 4-methoxybenzylmalonate, 2-ethylhexyl 4-methoxyphenylpropionate, 2-ethylhexyl 4-hydroxy-3,5-dimethoxyphenylpropionate, di-2-ethylhexyl 3,4,5-trimethoxybenzylmalonate, 2-ethylhexyl 4-hydroxy-3-methoxybenzylmalonate, di-2-ethylhexyl 4-hydroxy-3-methoxybenzylmalonate, di-2-ethylhexyl 3,4-dihydroxybenzylmalonate, 2-ethylhexyl 3,4-dihydroxyphenylpropionate, 3,4-dihydroxyphenylpropionic acid, phenethyl 3,4-dihydroxyphenylpropionate, 2-ethylhexyl 2-cyano-3,3-diphenylpropionate and oligo- and polysiloxanes which contain benzylmalonic acid derivatives or phenylpropionic acid derivatives, such as, preferably, diethyl p-benzylmalonate, bonded via propanyloxy, isopropanyloxy, propenyloxy, isopropenyloxy or allyloxy spacers.

It may be particularly preferred here for the compounds 2-ethylhexyl 4-hydroxy-3,5-di-t-butylphenylpropionate, ethyl 4-hydroxy-3,5-di-t-butylphenylpropionate, methyl 4-hydroxy-3,5-di-t-butylphenylpropionate, 2-ethylhexyl 4-hydroxy-3-t-butylphenylpropionate, ethyl 4-hydroxy-3-t-butylphenylpropionate, methyl 4-hydroxy-3-t-butylphenylpropionate, ethyl 4-hydroxy-3-methoxyphenylpropionate, methyl 4-hydroxy-3-methoxyphenylpropionate, ethyl 4-hydroxy-3,5-dimethoxyphenylpropionate, methyl 4-hydroxy-3,5-dimethoxyphenylpropionate, diethyl 4-hydroxy-3-methoxybenzylmalonate, diethyl 4-hydroxy-3,5-di-t-butylbenzylmalonate, dimethyl 4-hydroxy-3,5-di-t-butylbenzylmalonate not to be used in accordance with the invention.

It may furthermore be preferred in accordance with the invention for at least one compound of the formula I in which $Z^1$ stands for NH, and X stands for —C(=O)—$Z^2$—$R^1$, where the two radicals —$Z^2$—$R^1$ are identical, and $R^2$ to $R^6$ each, independently of one another, preferably stand for H, hydroxyl or methoxy, to be used.

Preference is furthermore given to the use of compounds of the formula I in which $Z^1$ stands for NH, and $R^1$ stands for a radical $R^a$ or $R^b$

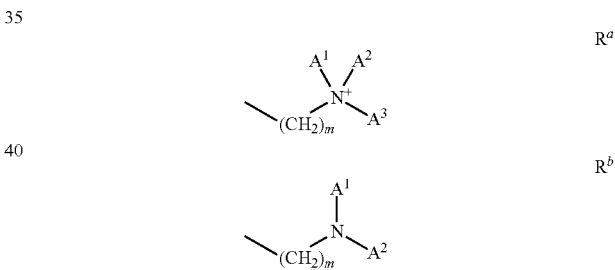

where m stands for an integer from the range from 1 to 3, and $A^1$-$A^3$ each, independently of one another, stand for a radical —$(CH_2)_o(O)_pH$, where o stands for 1, 2 or 3, and p stands for 0 or 1.

Particular preference is furthermore given in accordance with the invention to the use of compounds selected from compounds Ib to Iah and salts thereof, in particular chlorides thereof,

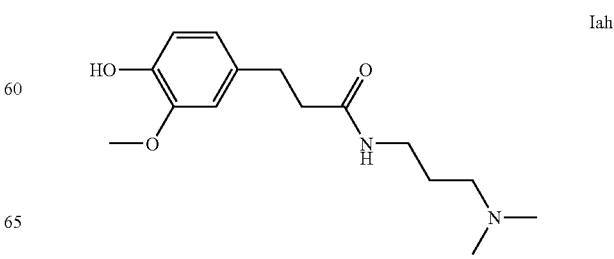

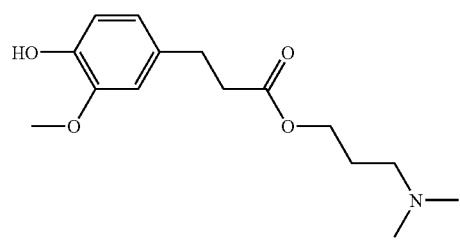 Ib
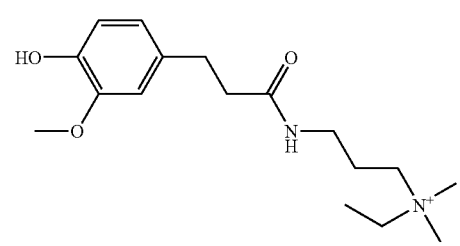 Ic
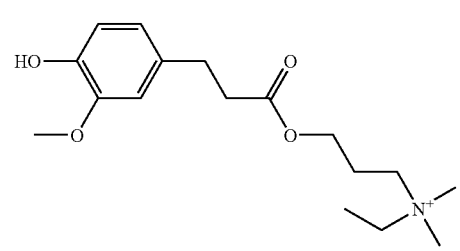 Id
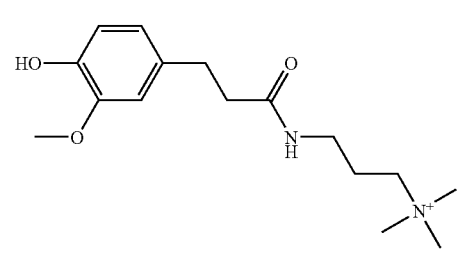 Ie
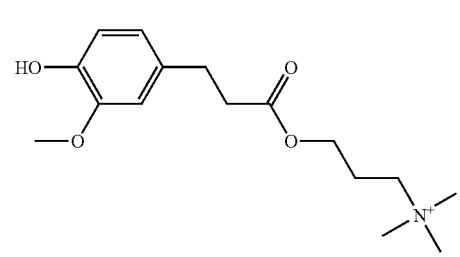 If
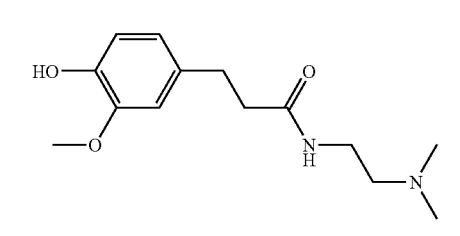 Ig
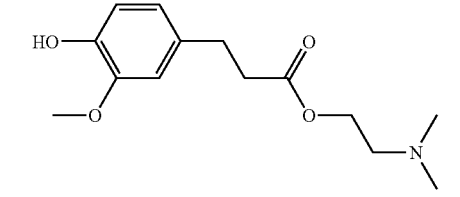 Ih
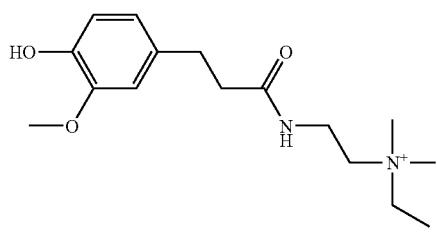 Ij
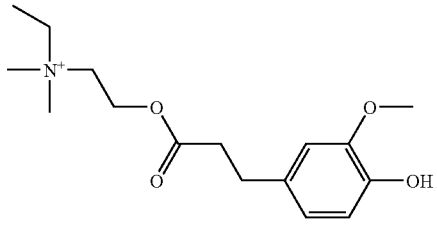 Ik
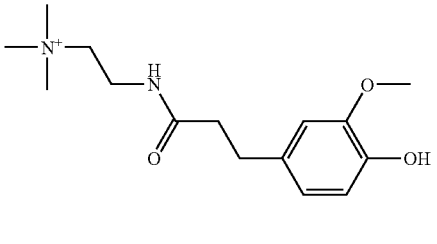 Im
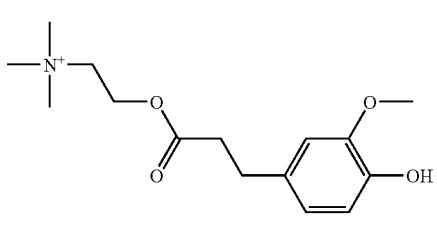 In
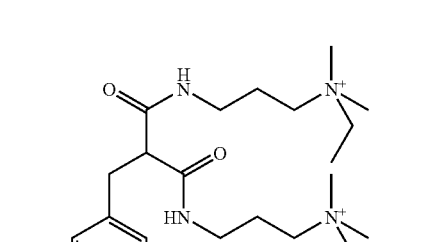 Io
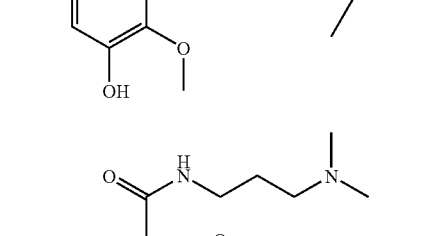 Ip

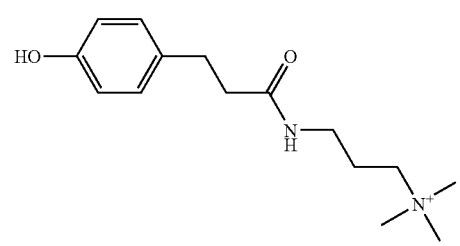
Iq
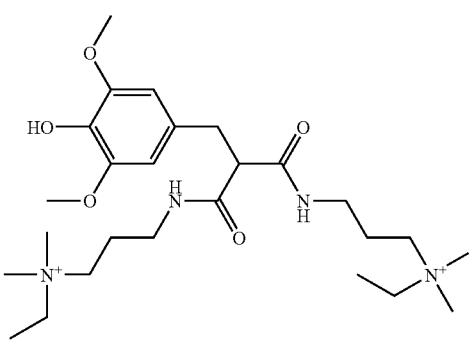
Ir
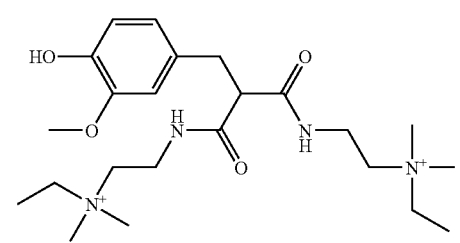
Is
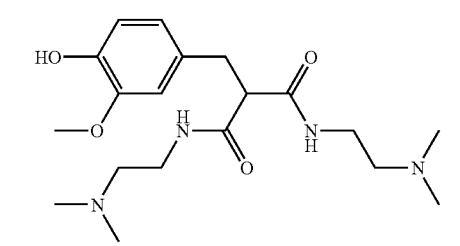
It
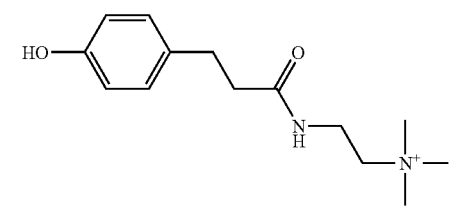
Iu
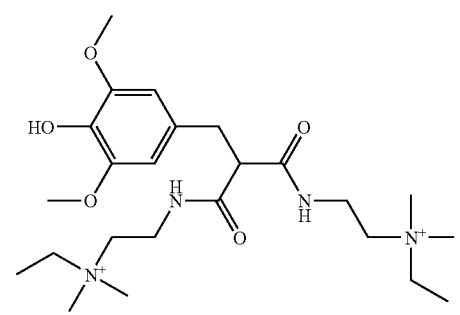
Iv
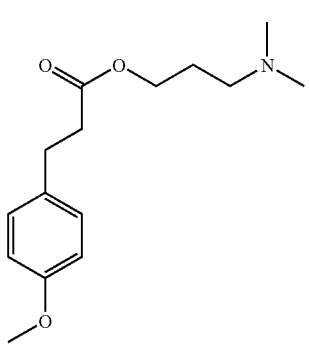
Iw
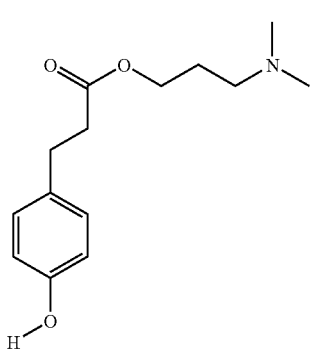
Ix
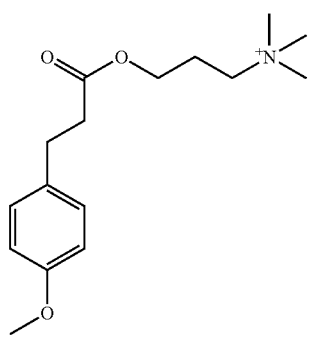
Iy
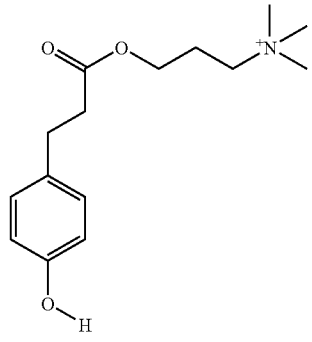
Iz -continued Iaa
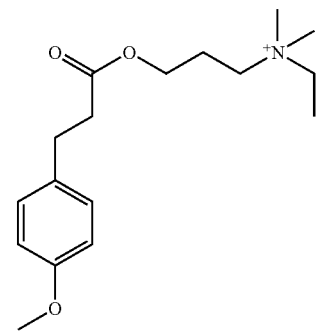

Iab
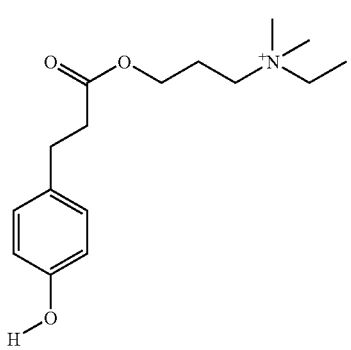

Iac
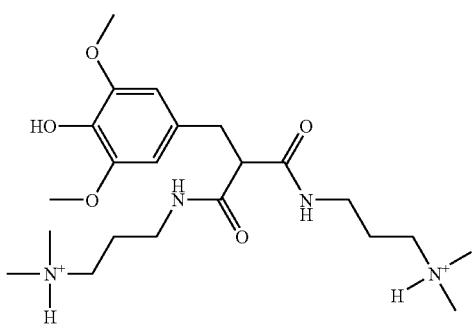

Iad
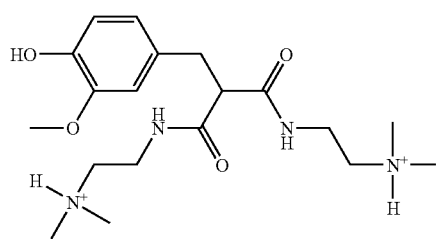

Iae
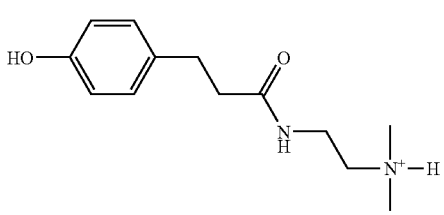

-continued

Iaf
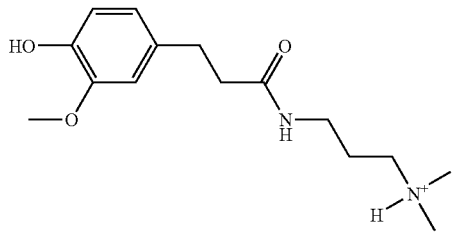

Iag
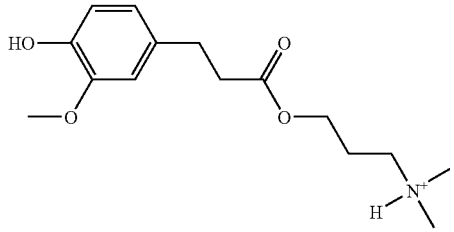

The invention furthermore relates to compositions comprising at least one compound of the formula I. The compositions are usually either compositions which can be applied topically, for example cosmetic or dermatological formulations, or foods or food supplements or domestic products. In this case, the compositions comprise a cosmetically or dermatologically, food-suitable or domestic product-suitable vehicle and, depending on the desired property profile, optionally further suitable ingredients.

Advantages of the compounds according to the invention or the use of compounds according to the invention or the compositions according to the invention may, in particular, be the following:

- the UV absorption that sets in on activation, in particular UV irradiation, can if necessary, for example in the case of intense UV radiation, increase the UV protection of the composition comprising them,
- preferred compounds of the formula I are suitable as oil component in compositions,
- preferred compounds of the formula I are suitable for improving the formulation properties, such as, for example, the skin feel, of compositions,
- preferred compounds of the formula I exhibit good solubility and solvent properties, preferably, for example, as solvents for crystalline components,
- a preferred group of compounds according to the invention can also cause skin tanning or improve the action of skin-tanning substances, such as dihydroxyacetone,
- well tolerated by the skin,
- in particular in the case of the ammonium compounds of the formula I, the adsorption behaviour onto keratinic fibres, such as, in particular, hair, is excellent,
- in the case of preferred compounds, an antioxidant action against free radicals, which are induced, for example, by UV light or thermolytic processes, such as smoking, such as, for example, against the superoxide free-radical anion or the NO free radical, or against reactive oxygen species, such as, for example, against singlet oxygen and peroxides,
- preferred compounds of the formula I are suitable for the production or boosting of light protection factors, such as LSF, SPF, PPD or IPD, or free-radical protection factors,
- a product-stabilising action on cosmetic, pharmaceutical, in particular dermatological products or domestic products or foods and food supplements, in particular those which comprise dyes, consistency substances or odour substances, a product-stabilising action on pigments and surface coatings, a stabilising action on autooxidisable polyethylene glycol (PEG) or polyglycerin (PG) derivatives, such as, in particular, PEG- or PG-containing emulsifiers, as mentioned below in this application, or a reduction in the damaging action of the degradation products of autooxidisable polyethylene glycol (PEG) or polyglycerin (PG) derivatives, a stabilising action on colorants, consistency substances or odour substances, or on antioxidants or vitamins, and UV filters as well as titanium dioxide-containing pigments, in particular in cosmetic, pharmaceutical, in particular dermatological products or domestic products or foods and food supplements, while most antioxidants become ineffective after reaction with free radicals, preferred compounds of the formula I exhibit a UV-filtering action after this reaction and thus continue their protective function, preferred compounds according to the invention having antioxidant properties can also be employed for pigmentation control since they can have a lightening action on skin areas.

It has furthermore been found that dyes, consistency substances or odour substances, or on antioxidants or vitamins, and UV filters as well as titanium dioxide-containing pigments can accelerate the conversion of preferred compounds of the formula I into the UV-absorbent oxidation products.

In addition, preferred compounds of those described here are colourless or only weakly coloured and thus do not result in discoloration of the compositions, or only do so to a minor extent.

As already stated above, the present invention furthermore relates to compositions comprising at least one vehicle which is suitable for cosmetic or dermatological compositions or domestic products and at least one compound which does not itself exhibit significant UV absorption in the UV-A or UV-B region, but is reactive under use conditions and develops UV-A or UV-B protection.

Preferred compositions here comprise the compounds of the formula I or Ia described in detail above.

It is particularly preferred in accordance with the invention for the composition to comprise at least one compound of the formula I ena or I enb

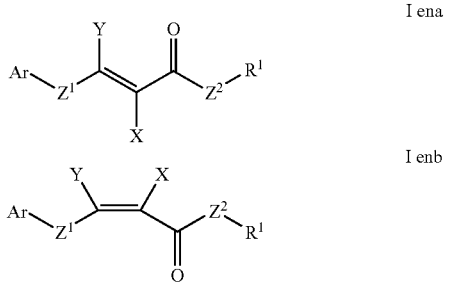

where the radicals Ar, X, Y, $Z^1$ and $Z^2$ and $R^1$ each, independently of one another and independently of the radicals of the compounds of the formula I, have the meaning indicated above for the compounds of the formula I.

It is particularly preferred here for the composition to comprise at least one compound of the formula Ia ena or Ia enb

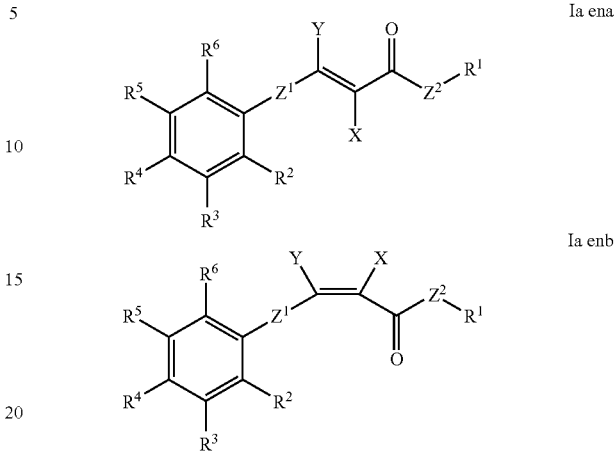

where the radicals X, Y, $Z^1$ and $Z^2$ and $R^1$-$R^6$ each, independently of one another and independently of the radicals of the compounds of the formula Ia, have the meaning indicated above for the compounds of the formula Ia.

It is particularly preferred here for the radicals X, Y, $Z^1$ and $Z^2$ and $R^1$-$R^6$ in the at least one compound of the formula I and the at least one compound of the formula I ena or I enb or the at least one compound of the formula Ia and the at least one compound of the formula Ia ena or Ia enb to be identical. In this case, the compound of the formula I or Ia can simultaneously serve as reservoir for the UV absorption potential of the compound of the formula I ena or I enb or Ia ena or Ia enb. In other words, the use of the compounds of the formula I or Ia thus facilitates a reduction in the use concentration of the UV filter of the formula I ena or I enb or Ia ena or Ia enb or the subsequent formation of the UV filter of the formula I ena or I enb or Ia ena or Ia enb by UV-induced oxidation of the compounds of the formula I can thus compensate for the loss in performance that many compounds of the formula I ena or I enb or Ia ena or Ia enb suffer on UV irradiation as a consequence of photoreactions or the subsequent formation of the UV filter of the formula I ena or I enb or Ia ena or Ia enb due to UV-induced oxidation of the compounds of the formula I or Ia can thus if necessary, i.e. in the case of intense UV radiation, increase the UV protection potential of the composition comprising them. The mixing ratio in which compounds of the formula I or Ia and compounds of the formula I ena or I enb or Ia ena or Ia enb are employed depends on the particular application (for example UV-induced UV protection boost or compensation for the UV-induced loss of action) and the photostability of the compounds of the formula I ena or I enb or Ia ena or Ia enb, where the adjustment of the use concentrations presents the person skilled in the art with absolutely no difficulties.

It is particularly preferred here for at least one compound of the formula I ena or I enb or Ia ena or Ia enb to be a compound selected from 4-hydroxycinnamic acid, 2-ethylhexyl 4-hydroxycinnamate, di-2-ethylhexyl 4-hydroxy-3,5-dimethoxybenzylidenemalonate, di-2-ethylhexyl 4-methoxybenzylidenemalonate, 2-ethylhexyl 4-methoxycinnamate, 2-ethylhexyl 4-hydroxy-3,5-dimethoxycinnamate, di-2-ethylhexyl 3,4,5-trimethoxybenzylidenemalonate, 2-ethylhexyl 4-hydroxy-3-methoxycinnamate, di-2-ethylhexyl 4-hydroxy-3-methoxybenzylidenemalonate, di-2-ethylhexyl 3,4- dihydroxybenzylidenemalonate, 2-ethylhexyl 3,4-dihydroxycinnamate, 3,4-dihydroxycinnamic acid, phenethyl 3,4-dihydroxycinnamate, 2-ethylhexyl 2-cyano-3-phenylcinnamate and oligo- and polysiloxanes which contain benzylidenemalonic acid derivatives or cinnamic acid derivatives, such as, preferably, diethyl p-benzylidenemalonate, bonded via propanyloxy, isopropanyloxy, propenyloxy, isopropenyloxy or allyloxy spacers.

The compounds which do not themselves exhibit significant UV absorption in the UV-A or UV-B region, but are reactive under use conditions and develop UV-A or UV-B protection are typically employed in accordance with the invention in amounts of 0.01 to 20% by weight, preferably in amounts of 0.1% by weight to 10% by weight and particularly preferably in amounts of 1 to 8% by weight. The person skilled in the art is presented with absolutely no difficulties in selecting the amounts appropriately depending on the intended action of the composition.

In order that the compounds according to the invention are able to develop their positive action as free-radical scavengers on the skin particularly well, it may be preferred to allow the compounds according to the invention to penetrate into deeper skin layers. Several possibilities are available for this purpose. Firstly, the compounds according to the invention can have an adequate lipophilicity in order to be able to penetrate through the outer skin layer into epidermal layers. As a further possibility, corresponding transport agents, for example liposomes, which enable transport of the compounds according to the invention through the outer skin layers may also be provided in the composition. Finally, systemic transport of the compounds according to the invention is also conceivable. The composition is then designed, for example, in such a way that it is suitable for oral administration.

In general, the substances of the formula I act as free-radical scavengers. Free radicals of this type are not generated exogenously only by sunlight, but also by the action of reactive substances, such as ozone, nitrogen oxides (for example cigarette smoke) or exposure to heavy metals (for example in the food). Further examples are anoxia, which blocks the flow of electrons upstream of the cytochrome oxidases and causes the formation of superoxide free-radical anions; inflammation associated, inter alia, with the formation of superoxide anions by the membrane NADPH oxidase of the leucocytes, but also associated with the formation (through disproportionation in the presence of iron(II) ions) of the hydroxyl free radicals and other reactive species which are normally involved in the phenomenon of phagocytosis; and lipid autoxidation, which is generally initiated by a hydroxyl free radical and produces lipidic alkoxy free radicals and hydroperoxides.

Owing to these properties, the compounds and compositions according to the invention are, in general, suitable for immune protection and for the protection of DNA and RNA. In particular, the compounds and compositions are suitable for the protection of DNA and RNA against oxidative attack, against free radicals and against damage due to radiation, in particular UV radiation. A further advantage of the compounds and compositions according to the invention is cell protection, in particular protection of Langerhans cells against damage due to the above-mentioned influences. All these uses and the use of the compounds according to the invention for the preparation of compositions which can be employed correspondingly are expressly also a subject-matter of the present invention.

In particular, preferred compounds and compositions according to the invention are also suitable for the treatment of skin diseases associated with a defect in keratinisation which affects differentiation and cell proliferation, in particular for the treatment of acne vulgaris, acne comedonica, polymorphic acne, acne rosaceae, nodular acne, acne conglobata, age-induced acne, acne which arises as a side effect, such as acne solaris, medicament-induced acne or acne professionalis, for the treatment of other defects in keratinisation, in particular ichthyosis, ichthyosiform states, Darier's disease, keratosis palmoplantaris, leukoplakia, leukoplakiform states, herpes of the skin and mucous membrane (buccal) (lichen), for the treatment of other skin diseases associated with a defect in keratinisation and which have an inflammatory and/or immunoallergic component and in particular all forms of psoriasis which affect the skin, mucous membranes and fingers and toenails, and psoriatic rheumatism and skin atopy, such as eczema or respiratory atopy, or hypertrophy of the gums, it furthermore being possible for the compounds to be used for some inflammation which is not associated with a defect in keratinisation, for the treatment of all benign or malignant excrescence of the dermis or epidermis, which may be of viral origin, such as verruca vulgaris, verruca plana, epidermodysplasia verruciformis, oral papillomatosis, papillomatosis florida, and excrescence which may be caused by UV radiation, in particular epithelioma baso-cellulare and epithelioma spinocellulare, for the treatment of other skin diseases, such as dermatitis bullosa and diseases affecting the collagen, for the treatment of certain eye diseases, in particular corneal diseases, for overcoming or combating light-induced skin ageing associated with ageing, for reducing pigmentation and keratosis actinica and for the treatment of all diseases associated with normal ageing or light-induced ageing, for the prevention or healing of wounds/scars of atrophy of the epidermis and/or dermis caused by locally or systemically applied corticosteroids and all other types of skin atrophy, for the prevention or treatment of defects in wound healing, for the prevention or elimination of stretch marks caused by pregnancy or for the promotion of wound healing, for combating defects in sebum production, such as hyperseborrhoea in acne or simple seborrhoea, for combating or preventing cancer-like states or pre-carcinogenic states, in particular promyelocytic leukaemia, for the treatment of inflammatory diseases, such as arthritis, for the treatment of all virus-induced diseases of the skin or other areas of the body, for the prevention or treatment of alopecia, for the treatment of skin diseases or diseases of other areas of the body with an immunological component, for the treatment of cardiovascular diseases, such as arteriosclerosis or hypertension, and of non-insulin-dependent diabetes, for the treatment of skin problems caused by UV radiation.

The antioxidant actions of the compounds of the formula I can be demonstrated, for example, by means of the 2,2-diphenyl-1-picrylhydrazyl (DPPH) assay. 2,2-Diphenyl-1-picrylhydrazyl is a free radical which is stable in solution. The unpaired electron results in a strong absorption band at 515 nm, and the solution has a dark-violet colour. In the presence of a free-radical scavenger, the electron is paired, the absorption disappears, and the decoloration proceeds stoichiometrically taking into account the electrons taken up. The absorbance is measured in a photometer. The anti-free-radical property of the substance to be tested is determined by measuring the concentration at which 50% of the 2,2-diphenyl-1-picrylhydrazyl employed has reacted with the free-radical scavenger. This concentration is expressed as $EC_{50}$, a value which should be regarded as a property of the substance under the given measurement conditions. The substance investigated is compared with a standard (for example tocopherol). The $EC_{50}$ value here is a measure of the capacity of the respective compound to scavenge free radicals. The lower the EC$_{50}$ value, the higher the capacity to scavenge free radicals. For the purposes of this invention, the expression "a large or high capacity to scavenge free radicals" is used if the EC$_{50}$ value is lower than that of tocopherol.

A further important aspect for the action of the antioxidants is the time in which this EC$_{50}$ value is achieved. This time, measured in minutes, gives the T$_{EC50}$ value, which allows a conclusion to be drawn on the rate at which these antioxidants scavenge free radicals. For the purposes of this invention, antioxidants which achieve this value within less than 60 minutes are regarded as fast, those which only achieve the EC$_{50}$ value after more than 120 minutes are regarded as having a delayed action.

The anti-free-radical efficiency (AE) (described in C. Sanchez-Moreno, J. A. Larrauri and F. Saura-Calixto in J. Sci. Food Agric. 1998, 76(2), 270-276) is given by the abovementioned quantities in accordance with the following relationship:

$$AE = \frac{1}{EC_{50} T_{EC50}}$$

A low AE ($\times 10^3$) is in the range up to about 10, a morate AE is in the range from 10 to 20 and a high AE has in accordance with the invention values above 20.

It may be particularly preferred in accordance with the invention to combine fast-acting antioxidants with those having a slow or time-delayed action. Typical weight ratios of the fast-acting antioxidants to time-delayed antioxidants are in the range from 10:1 to 1:10, preferably in the range from 10:1 to 1:1, and for skin-protecting compositions particularly preferably in the range from 5:1 to 2:1. In other compositions which are likewise preferred in accordance with the invention, it may, however, be advantageous for the purposes of action optimisation for more time-delayed antioxidants than fast-acting antioxidants to be present. Typical compositions then exhibit weight ratios of the fast-acting antioxidants to time-delayed antioxidants in the range from 1:1 to 1:10, preferably in the range from 1:2 to 1:8.

The protective action against oxidative stress or against the effect of free radicals can thus be further improved if the compositions comprise one or more further antioxidants, the person skilled in the art being presented with absolutely no difficulties in selecting suitably fast-acting or time-delayed anti oxidants.

In a preferred embodiment of the present invention, the composition is therefore a composition for the protection of body cells against oxidative stress, in particular for reducing skin ageing, characterised in that it preferably comprises one or more further antioxidants besides the one or more compounds of the formula I.

There are many proven substances known from the specialist literature which can be used as antioxidants, for example amino acids (for example glycine, histidine, tyrosine, tryptophan) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example α-carotene, β-carotene, lycopene) and derivatives thereof, chlorogenic acid and derivatives thereof, lipoic acid and derivatives thereof (for example dihydrolipoic acid), aurothioglucose, propylthiouracil and other thiols (for example thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts), and sulfoximine compounds (for example buthionine sulfoximines, homocysteine sulfoximine, buthionine sulfones, penta-, hexa- and heptathionine sulfoximine) in very low tolerated doses (for example pmol to μmol/kg), and also (metal) chelating agents, (for example α-hydroxy fatty acids, palmitic acid, phytic acid, lactoferrin), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof, vitamin C and derivatives (for example ascorbyl palmitate, magnesium ascorbyl phosphate, ascorbyl acetate), tocopherols and derivatives (for example vitamin E acetate), vitamin A and derivatives (for example vitamin A palmitate), and coniferyl benzoate of benzoin resin, rutinic acid and derivatives thereof, α-glycosyl rutin, ferulic acid, furfurylideneglucitol, carnosine, butylhydroxytoluene, butylhydroxyanisole, nordihydroguaiaretic acid, trihydroxybutyrophenone, quercetin, uric acid and derivatives thereof, mannose and derivatives thereof, zinc and derivatives thereof (for example ZnO, ZnSO$_4$), selenium and derivatives thereof (for example selenomethionine), stilbenes and derivatives thereof (for example stilbene oxide, trans-stilbene oxide).

Mixtures of antioxidants are likewise suitable for use in the cosmetic compositions according to the invention. Known and commercial mixtures are, for example, mixtures comprising, as active ingredients, lecithin, L-(+)-ascorbyl palmitate and citric acid (for example Oxynex® AP), natural tocopherols, L-(+)-ascorbyl palmitate, L-(+)-ascorbic acid and citric acid (for example Oxynex® K LIQUID), tocopherol extracts from natural sources, L-(+)-ascorbyl palmitate, L-(+)-ascorbic acid and citric acid (for example Oxynex® L LIQUID), DL-α-tocopherol, L-(+)-ascorbyl palmitate, citric acid and lecithin (for example Oxynex® LM) or butylhydroxytoluene (BHT), L-(+)-ascorbyl palmitate and citric acid (for example Oxynex® 2004). Antioxidants of this type are usually employed in such compositions with compounds according to the invention in ratios in the range from 1000:1 to 1:1000, preferably in amounts of 100:1 to 1:100.

The compositions according to the invention may comprise vitamins as further ingredients. The cosmetic compositions according to the invention preferably comprise vitamins and vitamin derivatives selected from vitamin A, vitamin A propionate, vitamin A palmitate, vitamin A acetate, retinol, vitamin B, thiamine chloride hydrochloride (vitamin B$_1$), riboflavin (vitamin B$_2$), nicotinamide, vitamin C (ascorbic acid), vitamin D, ergocalciferol (vitamin D$_2$), vitamin E, DL-α-tocopherol, tocopherol E acetate, tocopherol hydrogensuccinate, vitamin K$_1$, esculin (vitamin P active ingredient), thiamine (vitamin B$_1$), nicotinic acid (niacin), pyridoxine, pyridoxal, pyridoxamine (vitamin B$_6$), pantothenic acid, biotin, folic acid and cobalamine (vitamin B$_{12}$), particularly preferably vitamin A palmitate, retinol, vitamin C and derivatives thereof, DL-α-tocopherol, tocopherol E acetate, nicotinic acid, pantothenic acid and biotin. Vitamins are usually employed here with compounds according to the invention in ratios in the range from 1000:1 to 1:1000, preferably in amounts of 100:1 to 1:100.

It has been found here that antioxidants, such as, for example, beta-carotene and tocopherol, can accelerate the conversion of the compounds according to the invention into UV-filtering compounds. The present application therefore furthermore relates to the use of antioxidants for activating the compounds according to the invention.

The compounds according to the invention which are preferably to be employed in accordance with the invention generally have—after irradiation—a UV absorption in the UV-A and/or UV-B region. The compounds according to the invention which are to be employed in accordance with the invention include precursors of broadband UV filters, which can be employed alone or in combination with further UV filters. Other compounds according to the invention which are likewise preferred are precursors of UV filters having an absorption maximum in the boundary region between UV-B and UV-A radiation. As UV-A II filters, they therefore advantageously supplement the absorption spectrum of commercially available UV-B and UV-A I filters.

In addition, preferred compounds of this type have advantages on incorporation into the compositions:
  straight-chain or branched $C_1$- to $C_{20}$-alkoxy groups, in particular the long-chain alkoxy functions, such as ethylhexyloxy groups, increase the oil solubility of the compounds,
  in some cases, compounds of this type are in the form of oil components and can easily be incorporated into the composition or can function as solvent for other formulation constituents.

In likewise preferred embodiments of the invention, however, the compositions according to the invention may also comprise compounds according to the invention which have low solubility or are insoluble in the composition matrix. In this case, the compounds are preferably dispersed in the cosmetic composition in finely divided form.

Compositions which are particularly preferred in accordance with the invention also comprise pure UV filters in addition to the compounds according to the invention.

On use of the dibenzoylmethane derivatives, which are particularly preferred as UV-A filters, but are also used as UV-B filters, or the cinnamic acid derivatives, which are employed, in particular, as UV-B filters, in combination with the compounds according to the invention, an additional advantage arises: the UV-sensitive dibenzoylmethane derivatives and cinnamic acid derivatives are additionally stabilised by the presence of the compounds according to the invention. The present invention therefore furthermore relates to the use of the compounds of the formula I for the stabilisation of dibenzoylmethane derivatives and/or cinnamic acid derivatives in compositions.

In principle, all UV filters are suitable for combination with the compounds according to the invention. Particular preference is given to UV filters whose physiological acceptability has already been demonstrated. Both for UV-A and UV-B filters, there are many proven substances known from the specialist literature, for example
benzylidenecamphor derivatives, such as 3-(4'-methylbenzylidene)-dl-camphor (for example Eusolex® 6300), 3-benzylidenecamphor (for example Mexoryl® SD), polymers of N-{(2 and 4)-[(2-oxoborn-3-ylidene)methyl]-benzyl}acrylamide (for example Mexoryl® SW), N,N,N-trimethyl-4-(2-oxoborn-3-ylidenemethyl)anilinium methylsulfate (for example Mexoryl® SK) or (2-oxoborn-3-ylidene)toluene-4-sulfonic acid (for example Mexoryl® SL),
benzoyl- or dibenzoylmethanes, such as 1-(4-tert-butylphenyl)-3-(4-methoxyphenyl)propane-1,3-dione (for example Eusolex® 9020) or 4-isopropyldibenzoylmethane (for example Eusolex® 8020),
benzophenones, such as 2-hydroxy-4-methoxybenzophenone (for example Eusolex® 4360) or 2-hydroxy-4-methoxybenzophenone-5-sulfonic acid and its sodium salt (for example Uvinul® MS-40),
methoxycinnamic acid esters, such as octyl methoxycinnamate (for example Eusolex® 2292), isopentyl 4-methoxycinnamate, for example as a mixture of the isomers (for example Neo Heliopan® E 1000),
salicylate derivatives, such as 2-ethylhexyl salicylate (for example Eusolex® OS), 4-isopropylbenzyl salicylate (for example Megasol®) or 3,3,5-trimethylcyclohexyl salicylate (for example Eusolex® HMS),
4-aminobenzoic acid and derivatives, such as 4-aminobenzoic acid, 2-ethylhexyl 4-(dimethylamino)benzoate (for example Eusolex® 6007), ethoxylated ethyl 4-aminobenzoate (for example Uvinul® P25),
phenylbenzimidazolesulfonic acids, such as 2-phenylbenzimidazole-5-sulfonic acid and potassium, sodium and triethanolamine salts thereof (for example Eusolex® 232), 2,2-(1,4-phenylene)bisbenzimidazole-4,6-disulfonic acid and salts thereof (for example Neoheliopan® AP) or 2,2-(1,4-phenylene)bisbenzimidazole-6-sulfonic acid;
and further substances, such as
2-ethylhexyl 2-cyano-3,3-diphenylacrylate (for example Eusolex® OCR),
3,3'-(1,4-phenylenedimethylene)bis(7,7-dimethyl-2-oxobicyclo[2.2.1]hept-1-ylmethanesulfonic acid and salts thereof (for example Mexoryl® SX) and
2,4,6-trianilino-(p-carbo-2'-ethylhexyl-1'-oxy)-1,3,5-triazine (for example Uvinul® T 150)
hexyl 2-(4-diethylamino-2-hydroxybenzoyl)benzoate (for example Uvinul®UVA Plus, BASF).

The compounds mentioned in the list should only be regarded as examples. It is of course also possible to use other UV filters.

These organic UV filters are generally incorporated into cosmetic formulations in an amount of 0.5 to 10 percent by weight, preferably 1-8%.

Further suitable organic UV filters are, for example,
2-(2H-benzotriazol-2-yl)-4-methyl-6-(2-methyl-3-(1,3,3,3-tetramethyl-1-(trimethylsilyloxy)disiloxanyl)propyl)phenol (for example Silatrizole®),
2-ethylhexyl 4,4'-[(6-[4-((1,1-dimethylethyl)aminocarbonyl)phenylamino]-1,3,5-triazine-2,4-diyl)diimino]bis(benzoate) (for example Uvasorb® HEB),
α-(trimethylsilyl)-ω-[trimethylsilyl)oxy]poly[oxy(dimethyl [and approximately 6% of methyl[2-[p-[2,2-bis(ethoxycarbonyl]vinyl]phenoxy]-1-methyleneethyl] and approximately 1.5% of methyl[3-[p-[2,2-bis(ethoxycarbonyl)vinyl]phenoxy)propenyl) and 0.1 to 0.4% of (methylhydrogen]-silylene]] (n≈60) (CAS No. 207 574-74-1)
2,2'-methylenebis(6-(2H-benzotriazol-2-yl)-4-(1,1,3,3-tetramethylbutyl)phenol) (CAS No. 103 597-45-1)
2,2'-(1,4-phenylene)bis(1H-benzimidazole-4,6-disulfonic acid, monosodium salt) (CAS No. 180 898-37-7) and
2,4-bis{[4-(2-ethylhexyloxy)-2-hydroxy]phenyl}-6-(4-methoxyphenyl)-1,3,5-triazine (CAS No. 103 597-45-, 187 393-00-6).
2-ethylhexyl 4,4'-[(6-[4-((1,1-dimethylethyl)aminocarbonyl)phenylamino]-1,3,5-triazine-2,4-diyl)diimino]bis(benzoate) (for example Uvasorb® HEB), Further suitable UV filters are also methoxyflavones corresponding to the earlier German patent application DE-A-10232595.

Organic UV filters are generally incorporated into cosmetic formulations in an amount of 0.5 to 20 percent by weight, preferably 1-15%.

Conceivable inorganic UV filters are those from the group of the titanium dioxides, such as, for example, coated titanium dioxide (for example Eusolex® T-2000, Eusolex®

T-AQUA, Eusolex® T-AVO), zinc oxides (for example Sachtotec®), iron oxides or also cerium oxides. These inorganic UV filters are generally incorporated into cosmetic compositions in an amount of 0.5 to 20 percent by weight, preferably 2-10%.

Preferred compounds having UV-filtering properties are 3-(4'-methylbenzylidene)-dl-camphor, 1-(4-tert-butylphenyl)-3-(4-methoxyphenyl)propane-1,3-dione, 4-isopropyldibenzoylmethane, 2-hydroxy-4-methoxybenzophenone, octyl methoxycinnamate, 3,3,5-trimethylcyclohexyl salicylate, 2-ethylhexyl 4-(dimethylamino)benzoate, 2-ethylhexyl 2-cyano-3,3-diphenylacrylate, 2-phenylbenzimidazole-5-sulfonic acid and the potassium, sodium and triethanolamine salts thereof.

Combination of one or more compounds according to the invention with further UV filters enables the protective action against damaging effects of UV radiation to be optimised.

Optimised compositions may comprise, for example, the combination of the organic UV filters 4'-methoxy-6-hydroxyflavone with 1-(4-tert-butylphenyl)-3-(4-methoxyphenyl) propane-1,3-dione and 3-(4'-methylbenzylidene)-dl-camphor. This combination gives rise to broad-band protection, which can be supplemented by the addition of inorganic UV filters, such as titanium dioxide microparticles.

All the said UV filters and the compounds according to the invention can also be employed in encapsulated form. In particular, it is advantageous to employ organic UV filters in encapsulated form. In detail, the following advantages arise:

The hydrophilicity of the capsule wall can be set independently of the solubility of the UV filter or the compound of the formula I. Thus, for example, it is also possible to incorporate hydrophobic UV filters or compounds according to the invention into purely aqueous compositions. In addition, the oily impression on application of the composition comprising hydrophobic UV filters, which is frequently regarded as unpleasant, is suppressed.

Certain UV filters, in particular dibenzoylmethane derivatives, exhibit only reduced photostability in cosmetic compositions. Encapsulation of these filters or compounds which impair the photostability of these filters, such as, for example, cinnamic acid derivatives, enables the photostability of the entire composition to be increased.

Skin penetration by organic UV filters and the associated potential for irritation on direct application to the human skin is repeatedly being discussed in the literature. The encapsulation of the corresponding substances which is proposed here suppresses this effect.

In general, encapsulation of individual UV filters or compounds according to the invention or other ingredients enables composition problems caused by the interaction of individual composition constituents with one another, such as crystallisation processes, precipitation and agglomerate formation, to be avoided since the interaction is suppressed.

It is therefore preferred in accordance with the invention for one or more of the above-mentioned UV filters or compounds according to the invention to be in encapsulated form. It is advantageous here for the capsules to be so small that they cannot be viewed with the naked eye. In order to achieve the above-mentioned effects, it is furthermore necessary for the capsules to be sufficiently stable and the encapsulated active ingredient (UV filter) only to be released to the environment to a small extent, or not at all.

Suitable capsules can have walls of inorganic or organic polymers. For example, U.S. Pat. No. 6,242,099 B1 describes the production of suitable capsules with walls of chitin, chitin derivatives or polyhydroxylated polyamines. Capsules which can particularly preferably be employed in accordance with the invention have walls which can be obtained by a sol-gel process, as described in the applications WO 00/09652, WO 00/72806 and WO 00/71084. Preference is again given here to capsules whose walls are built up from silica gel (silica; undefined silicon oxide hydroxide). The production of corresponding capsules is known to the person skilled in the art, for example from the cited patent applications, whose contents expressly also belong to the subject-matter of the present application.

The capsules in compositions according to the invention are preferably present in amounts which ensure that the encapsulated UV filters are present in the composition in the above-indicated amounts.

The compositions according to the invention may in addition comprise further conventional skin-protecting or skin-care active ingredients. These may in principle be any active ingredients known to the person skilled in the art.

Particularly preferred active ingredients are pyrimidinecarboxylic acids and/or aryl oximes.

Pyrimidinecarboxylic acids occur in halophilic microorganisms and play a role in osmoregulation of these organisms (E. A. Galinski et al., Eur. J. Biochem., 149 (1985) pages 135-139). Of the pyrimidinecarboxylic acids, particular mention should be made here of ectoin ((S)-1,4,5,6-tetrahydro-2-methyl-4-pyrimidinecarboxylic acid) and hydroxyectoin ((S,S)-1,4,5,6-tetrahydro-5-hydroxy-2-methyl-4-pyrimidinecarboxylic acid and derivatives thereof. These compounds stabilise enzymes and other biomolecules in aqueous solutions and organic solvents. Furthermore, they stabilise, in particular, enzymes against denaturing conditions, such as salts, extreme pH values, surfactants, urea, guanidinium chloride and other compounds.

Ectoin and ectoin derivatives, such as hydroxyectoin, can advantageously be used in medicaments. In particular, hydroxyectoin can be employed for the preparation of a medicament for the treatment of skin diseases. Other areas of application of hydroxyectoin and other ectoin derivatives are typically in areas in which, for example, trehalose is used as additive. Thus, ectoin derivatives, such as hydroxyectoin, can be used as protectant in dried yeast and bacterial cells. Pharmaceutical products, such as non-glycosylated, pharmaceutically active peptides and proteins, for example t-PA, can also be protected with ectoin or its derivatives.

Of the cosmetic applications, particular mention should be made of the use of ectoin and ectoin derivatives for the care of aged, dry or irritated skin. Thus, European patent application EP-A-0 671 161 describes, in particular, that ectoin and hydroxyectoin are employed in cosmetic compositions, such as powders, soaps, surfactant-containing cleansing products, lipsticks, rouge, make-up, care creams and sunscreen preparations.

Preference is given here to the use of a pyrimidinecarboxylic acid of the following formula

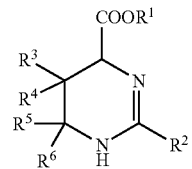

in which $R^1$ is a radical H or C1-8-alkyl, $R^2$ is a radical H or C1-4-alkyl, and $R^3$, $R^4$, $R^5$ and $R^6$ are each, independently of one another, a radical from the group H, OH, $NH_2$ and C1-4-alkyl. Preference is given to the use of pyrimidinecarboxylic acids in which $R^2$ is a methyl or ethyl group, and $R^1$ or $R^5$ and $R^6$ are H. Particular preference is given to the use of the pyrimidinecarboxylic acids ectoin ((S)-1,4,5,6-tetrahydro-2-methyl-4-pyrimidinecarboxylic acid) and hydroxyectoin ((S,S)-1,4,5,6-tetrahydro-5-hydroxy-2-methyl-4-pyrimidinecarboxylic acid). The compositions according to the invention preferably comprise pyrimidinecarboxylic acids of this type in amounts of up to 15% by weight. The pyrimidinecarboxylic acids are preferably employed here in ratios of 100:1 to 1:100 with respect to the compounds according to the invention, with ratios in the range 1:10 to 10:1 being particularly preferred.

Of the aryl oximes, preference is given to the use of 2-hydroxy-5-methyllaurophenone oxime, which is also known as HMLO, LPO or F5. Its suitability for use in cosmetic compositions is disclosed, for example, in DE-A-41 16 123. Compositions which comprise 2-hydroxy-5-methyllaurophenone oxime are accordingly suitable for the treatment of skin diseases which are accompanied by inflammation. It is known that compositions of this type can be used, for example, for the therapy of psoriasis, various forms of eczema, irritative and toxic dermatitis, UV dermatitis and further allergic and/or inflammatory diseases of the skin and skin appendages. Compositions according to the invention which, in addition to the compound of the formula I, additionally comprise an aryl oxime, preferably 2-hydroxy-5-methyllaurophenone oxime, exhibit surprising antiinflammatory suitability. The compositions here preferably comprise 0.01 to 10% by weight of the aryl oxime, it being particularly preferred for the composition to comprise 0.05 to 5% by weight of aryl oxime.

In a further, likewise preferred embodiment of the present invention, the composition according to the invention comprises at least one self-tanning agent.

Advantageous self-tanning agents which can be employed are, inter alia, trioses and tetroses, such as, for example, the following compounds:

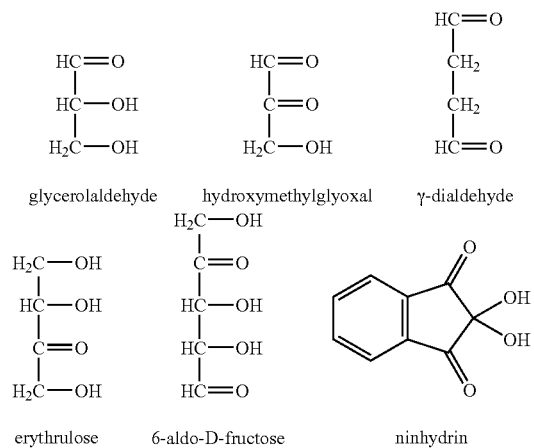

Mention should also be made of 5-hydroxy-1,4-naphthoquinone (juglone), which can be extracted from the shells of fresh walnuts, and 2-hydroxy-1,4-naphthoquinone (lawsone), which occurs in henna leaves. The flavonoid diosmetin and its glycosides or sulfates can also be employed. These compounds can be employed here in the form of pure substances or plant extracts. Diosmetin can preferably be employed, for example, in the form of a chrysanthemum extract.

Very particular preference is given to 1,3-dihydroxyacetone (DHA), a trifunctional sugar which occurs in the human body, and derivatives thereof.

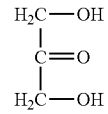

1,3-dihydroxyacetone (DHA)

The said self-tanning agents can be employed alone or as a mixture. It is particularly preferred here for DHA to be employed in a mixture with a further self-tanning agent of those mentioned above.

It has been found that the combination of self-tanning agents with the compounds according to the invention results in accelerated tanning compared with the use of the self-tanning agents alone. The present invention therefore furthermore relates to the corresponding use of the compounds according to the invention for accelerating the tanning action of self-tanning agents.

All compounds or components which can be used in the compositions are either known and commercially available or can be synthesised by known processes.

The one or more compounds according to the invention can be incorporated into cosmetic or dermatological compositions in the customary manner. Suitable compositions are those for external use, for example in the form of a cream, lotion, gel or as a solution which can be sprayed onto the skin. Suitable for internal use are administration forms such as capsules, coated tablets, powders, tablet solutions or solutions.

Examples which may be mentioned of application forms of the compositions according to the invention are: solutions, suspensions, emulsions, PIT emulsions, pastes, ointments, gels, creams, lotions, powders, soaps, surfactant-containing cleansing preparations, oils, aerosols and sprays.

Examples of other application forms are sticks, shampoos and shower compositions. Any desired customary vehicles, auxiliaries and, if desired, further active ingredients may be added to the composition.

Preferred auxiliaries originate from the group of the preservatives, antioxidants, stabilisers, solubilisers, vitamins, colorants, odour improvers.

Ointments, pastes, creams and gels may comprise the customary vehicles, for example animal and vegetable fats, waxes, paraffins, starch, tragacanth, cellulose derivatives, polyethylene glycols, silicones, bentonites, silica, talc and zinc oxide, or mixtures of these substances.

Powders and sprays may comprise the customary vehicles, for example lactose, talc, silica, aluminium hydroxide, calcium silicate and polyamide powder, or mixtures of these substances. Sprays may additionally comprise the customary propellants, for example chlorofluorocarbons, propane/butane or dimethyl ether.

Solutions and emulsions may comprise the customary vehicles, such as solvents, solubilisers and emulsifiers, for example water, ethanol, isopropanol, ethyl carbonate, ethyl acetate, benzyl alcohol, benzyl benzoate, propylene glycol, 1,3-butyl glycol, oils, in particular cottonseed oil, peanut oil, wheatgerm oil, olive oil, castor oil and sesame oil, glycerol fatty acid esters, polyethylene glycols and fatty acid esters of sorbitan, or mixtures of these substances.

Suspensions may comprise the customary vehicles, such as liquid diluents, for example water, ethanol or propylene glycol, suspension media, for example ethoxylated isostearyl alcohols, polyoxyethylene sorbitol esters and polyoxyethylene sorbitan esters, microcrystalline cellulose, aluminium metahydroxide, bentonite, agar-agar and tragacanth, or mixtures of these substances.

Soaps may comprise the customary vehicles, such as alkali metal salts of fatty acids, salts of fatty acid monoesters, fatty acid protein hydrolysates, isothionates, lanolin, fatty alcohol, vegetable oils, plant extracts, glycerol, sugars, or mixtures of these substances.

Surfactant-containing cleansing products may comprise the customary vehicles, such as salts of fatty alcohol sulfates, fatty alcohol ether sulfates, sulfosuccinic acid monoesters, fatty acid protein hydrolysates, isothionates, imidazolinium derivatives, methyl taurates, sarcosinates, fatty acid amide ether sulfates, alkylamidobetaines, fatty alcohols, fatty acid glycerides, fatty acid diethanolamides, vegetable and synthetic oils, lanolin derivatives, ethoxylated glycerol fatty acid esters, or mixtures of these substances.

Face and body oils may comprise the customary vehicles, such as synthetic oils, such as fatty acid esters, fatty alcohols, silicone oils, natural oils, such as vegetable oils and oily plant extracts, paraffin oils, lanolin oils, or mixtures of these substances.

Further typical cosmetic application forms are also lipsticks, lip-care sticks, mascara, eyeliner, eye shadow, rouge, powder make-up, emulsion make-up and wax make-up, and sunscreen, pre-sun and after-sun preparations.

The preferred composition forms according to the invention include, in particular, emulsions.

Emulsions according to the invention are advantageous and comprise, for example, the said fats, oils, waxes and other fatty substances, as well as water and an emulsifier, as usually used for a composition of this type.

The lipid phase may advantageously be selected from the following group of substances:
 mineral oils, mineral waxes;
 oils, such as triglycerides of capric or caprylic acid, furthermore natural oils, such as, for example, castor oil;
 fats, waxes and other natural and synthetic fatty substances, preferably esters of fatty acids with alcohols having a low carbon number, for example with isopropanol, propylene glycol or glycerol, or esters of fatty alcohols with alkanoic acids having a low carbon number or with fatty acids;
 silicone oils, such as dimethylpolysiloxanes, diethylpolysiloxanes, diphenylpolysiloxanes and mixed forms thereof.

For the purposes of the present invention, the oil phase of the emulsions, oleogels or hydrodispersions or lipodispersions is advantageously selected from the group of the esters of saturated and/or unsaturated, branched and/or unbranched alkanecarboxylic acids having a chain length of 3 to 30 C atoms and saturated and/or unsaturated, branched and/or unbranched alcohols having a chain length of 3 to 30 C atoms, or from the group of the esters of aromatic carboxylic acids and saturated and/or unsaturated, branched and/or unbranched alcohols having a chain length of 3 to 30 C atoms. Ester oils of this type can then advantageously be selected from the group isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate and synthetic, semi-synthetic and natural mixtures of esters of this type, for example jojoba oil.

The oil phase may furthermore advantageously be selected from the group of the branched and unbranched hydrocarbons and waxes, silicone oils, dialkyl ethers, the group of the saturated or unsaturated, branched or unbranched alcohols, and fatty acid triglycerides, specifically the triglycerol esters of saturated and/or unsaturated, branched and/or unbranched alkanecarboxylic acids having a chain length of 8 to 24, in particular 12-18, C atoms. The fatty acid triglycerides may advantageously be selected, for example, from the group of the synthetic, semi-synthetic and natural oils, for example olive oil, sunflower oil, soya oil, peanut oil, rapeseed oil, almond oil, palm oil, coconut oil, palm kernel oil and the like.

Any desired mixtures of oil and wax components of this type may also advantageously be employed for the purposes of the present invention. It may also be advantageous to employ waxes, for example cetyl palmitate, as the only lipid component of the oil phase.

The oil phase is advantageously selected from the group 2-ethylhexyl isostearate, octyldodecanol, isotridecyl isononanoate, isoeicosane, 2-ethylhexyl cocoate, $C_{12-15}$-alkyl benzoate, caprylic/capric acid triglyceride and dicapryl ether.

Particularly advantageous are mixtures of $C_{12-15}$-alkyl benzoate and 2-ethylhexyl isostearate, mixtures of $C_{12-15}$-alkyl benzoate and isotridecyl isononanoate, as well as mixtures of $C_{12-15}$-alkyl benzoate, 2-ethylhexyl isostearate and isotridecyl isononanoate.

Of the hydrocarbons, paraffin oil, squalane and squalene may advantageously be used for the purposes of the present invention.

Furthermore, the oil phase may also advantageously have a content of cyclic or linear silicone oils or consist entirely of oils of this type, although it is preferred to use an additional content of other oil-phase components in addition to the silicone oil or the silicone oils.

The silicone oil to be used in accordance with the invention is advantageously cyclomethicone (octamethylcyclotetrasiloxane). However, it is also advantageous for the purposes of the present invention to use other silicone oils, for example hexamethylcyclotrisiloxane, polydimethylsiloxane or poly (methylphenylsiloxane).

Also particularly advantageous are mixtures of cyclomethicone and isotridecyl isononanoate, of cyclomethicone and 2-ethylhexyl isostearate.

The aqueous phase of the compositions according to the invention optionally advantageously comprises alcohols, diols or polyols having a low carbon number, and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, furthermore alcohols having a low carbon number, for example ethanol, isopropanol, 1,2-propanediol, glycerol, and, in particular, one or more thickeners, which may advantageously be selected from the group silicon dioxide, aluminium silicates, polysaccharides and derivatives thereof, for example hyaluronic acid, xanthan gum, hydroxypropylmethylcellulose, particularly advantageously from the group of the polyacrylates, preferably a polyacrylate from the group of the so-called Carbopols, for example Carbopol grades 980, 981, 1382, 2984 or 5984, in each case individually or in combination.

In particular, mixtures of the above-mentioned solvents are used. In the case of alcoholic solvents, water may be a further constituent.

Emulsions according to the invention are advantageous and comprise, for example, the said fats, oils, waxes and other fatty substances, as well as water and an emulsifier, as usually used for a formulation of this type.

In a preferred embodiment, the compositions according to the invention comprise hydrophilic surfactants.

The hydrophilic surfactants are preferably selected from the group of the alkylglucosides, acyl lactylates, betaines and coconut amphoacetates.

The alkylglucosides are themselves advantageously selected from the group of the alkylglucosides which are distinguished by the structural formula

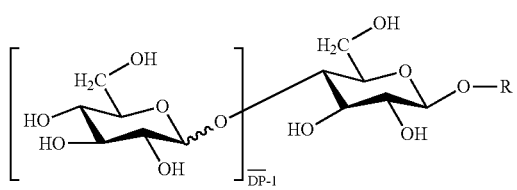

where R represents a branched or unbranched alkyl radical having 4 to 24 carbon atoms, and where $\overline{DP}$ denotes a mean degree of glucosylation of up to 2.

The value $\overline{DP}$ represents the degree of glucosidation of the alkylglucosides used in accordance with the invention and is defined as $$\overline{DP} = \frac{p_1}{100} \cdot 1 + \frac{p_2}{100} \cdot 2 + \frac{p_3}{100} \cdot 3 + \ldots = \sum \frac{p_i}{100} \cdot i$$

in which $p_1, p_2, p_3 \ldots p_i$ represent the proportion of mono-, di-, tri- . . . i-fold glucosylated products in percent by weight. Advantageous in accordance with the invention is the selection of products having degrees of glucosylation of 1-2, particularly advantageously of 1.1 to 1.5, very particularly advantageously of 1.2-1.4, in particular of 1.3.

The value DP takes into account the fact that alkylglucosides are generally, as a consequence of their preparation, in the form of mixtures of mono- and oligoglucosides. A relatively high content of monoglucosides, typically in the order of 40-70% by weight, is advantageous in accordance with the invention.

Alkylglycosides which are particularly advantageously used in accordance with the invention are selected from the group octyl glucopyranoside, nonyl glucopyranoside, decyl glucopyranoside, undecyl glucopyranoside, dodecyl glucopyranoside, tetradecyl glucopyranoside and hexadecyl glucopyranoside.

It is likewise advantageous to employ natural or synthetic raw materials and auxiliaries or mixtures which are distinguished by an effective content of the active ingredients used in accordance with the invention, for example Plantaren® 1200 (Henkel KGaA), Oramix® NS 10 (Seppic).

The acyllactylates are themselves advantageously selected from the group of the substances which are distinguished by the structural formula

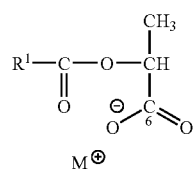

where $R^1$ denotes a branched or unbranched alkyl radical having 1 to 30 carbon atoms, and $M^+$ is selected from the group of the alkali metal ions and the group of ammonium ions which are substituted by one or more alkyl and/or one or more hydroxyalkyl radicals, or corresponds to half an equivalent of an alkaline earth metal ion.

For example, sodium isostearyl lactylate, for example the product Pathionic® ISL from the American Ingredients Company, is advantageous.

The betaines are advantageously selected from the group of the substances which are distinguished by the structural formula

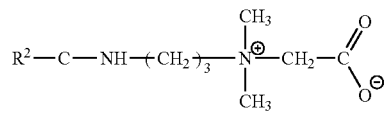

where $R^2$ denotes a branched or unbranched alkyl radical having 1 to 30 carbon atoms.

$R^2$ particularly advantageously denotes a branched or unbranched alkyl radical having 6 to 12 carbon atoms.

For example, capramidopropylbetaine, for example the product Tego® Betain 810 from Th. Goldschmidt AG, is advantageous.

A coconut amphoacetate which is advantageous in accordance with the invention is, for example, sodium coconut amphoacetate, as available under the name Miranol® Ultra C32 from Miranol Chemical Corp.

The compositions according to the invention are advantageously characterised in that the hydrophilic surfactant(s) is (are) present in concentrations of 0.01-20% by weight, preferably 0.05-10% by weight, particularly preferably 0.1-5% by weight, in each case based on the total weight of the composition.

For use, the cosmetic and dermatological compositions according to the invention are applied to the skin and/or the hair in an adequate amount in the usual manner for cosmetics.

Cosmetic and dermatological compositions according to the invention may exist in various forms. Thus, they may be, for example, a solution, a water-free composition, an emulsion or microemulsion of the water-in-oil (W/O) type or of the oil-in-water (O/W) type, a multiple emulsion, for example of the water-in-oil-in-water (W/O/W) type, a gel, a solid stick, an ointment or an aerosol. It is also advantageous to administer active ingredients in encapsulated form, for example in collagen matrices and other conventional encapsulation materials, for example as cellulose encapsulations, in gelatine, wax matrices or liposomally encapsulated. In particular, wax matrices, as described in DE-A 43 08 282, have proven favourable. Preference is given to emulsions. O/W emulsions are particularly preferred. Emulsions, W/O emulsions and O/W emulsions are obtainable in a conventional manner.

Emulsifiers that can be used are, for example, the known W/O and O/W emulsifiers. It is advantageous to use further conventional co-emulsifiers in the preferred O/W emulsions according to the invention.

Co-emulsifiers which are advantageous in accordance with the invention are, for example, O/W emulsifiers, principally from the group of the substances having HLB values of 11-16, very particularly advantageously having HLB values of 14.5-15.5, so long as the O/W emulsifiers have saturated radicals R and R'. If the O/W emulsifiers have unsaturated radicals R and/or R' or in the case of isoalkyl derivatives, the preferred HLB value of such emulsifiers may also be lower or higher.

It is advantageous to select the fatty alcohol ethoxylates from the group of ethoxylated stearyl alcohols, cetyl alcohols, cetylstearyl alcohols (cetearyl alcohols). Particular preference is given to the following: polyethylene glycol (13) stearyl ether (steareth-13), polyethylene glycol (14) stearyl ether (steareth-14), polyethylene glycol (15) stearyl ether (steareth-15), polyethylene glycol (16) stearyl ether (steareth-16), polyethylene glycol (17) stearyl ether (steareth-17), polyethylene glycol (18) stearyl ether (steareth-18), polyethylene glycol (19) stearyl ether (steareth-19), polyethylene glycol (20) stearyl ether (steareth-20), polyethylene glycol (12) isostearyl ether (isosteareth-12), polyethylene glycol (13) isostearyl ether (isosteareth-13), polyethylene glycol (14) isostearyl ether (isosteareth-14), polyethylene glycol (15) isostearyl ether (isosteareth-15), polyethylene glycol (16) isostearyl ether (isosteareth-16), polyethylene glycol (17) isostearyl ether (isosteareth-17), polyethylene glycol (18) isostearyl ether (isosteareth-18), polyethylene glycol (19) isostearyl ether (isosteareth-19), polyethylene glycol (20) isostearyl ether (isosteareth-20), polyethylene glycol (13) cetyl ether (ceteth-13), polyethylene glycol (14) cetyl ether (ceteth-14), polyethylene glycol (15) cetyl ether (ceteth-15), polyethylene glycol (16) cetyl ether (ceteth-16), polyethylene glycol (17) cetyl ether (ceteth-17), polyethylene glycol (18) cetyl ether (ceteth-18), polyethylene glycol (19) cetyl ether (ceteth-19), polyethylene glycol (20) cetyl ether (ceteth-20), polyethylene glycol (13) isocetyl ether (isoceteth-13), polyethylene glycol (14) isocetyl ether (isoceteth-14), polyethylene glycol (15) isocetyl ether (isoceteth-15), polyethylene glycol (16) isocetyl ether (isoceteth-16), polyethylene glycol (17) isocetyl ether (isoceteth-17), polyethylene glycol (18) isocetyl ether (isoceteth-18), polyethylene glycol (1 g) isocetyl ether (isoceteth-19), polyethylene glycol (20) isocetyl ether (isoceteth-20), polyethylene glycol (12) oleyl ether (oleth-12), polyethylene glycol (13) oleyl ether (oleth-13), polyethylene glycol (14) oleyl ether (oleth-14), polyethylene glycol (15) oleyl ether (oleth-15), polyethylene glycol (12) lauryl ether (laureth-12), polyethylene glycol (12) isolauryl ether (isolaureth-12), polyethylene glycol (13) cetylstearyl ether (ceteareth-13), polyethylene glycol (14) cetylstearyl ether (ceteareth-14), polyethylene glycol (15) cetylstearyl ether (ceteareth-15), polyethylene glycol (16) cetylstearyl ether (ceteareth-16), polyethylene glycol (17) cetylstearyl ether (ceteareth-17), polyethylene glycol (18) cetylstearyl ether (ceteareth-18), polyethylene glycol (19) cetylstearyl ether (ceteareth-1 g), polyethylene glycol (20) cetylstearyl ether (ceteareth-20).

It is furthermore advantageous to select the fatty acid ethoxylates from the following group:
polyethylene glycol (20) stearate, polyethylene glycol (21) stearate, polyethylene glycol (22) stearate, polyethylene glycol (23) stearate, polyethylene glycol (24) stearate, polyethylene glycol (25) stearate, polyethylene glycol (12) isostearate, polyethylene glycol (13) isostearate, polyethylene glycol (14) isostearate, polyethylene glycol (15) isostearate, polyethylene glycol (16) isostearate, polyethylene glycol (17) isostearate, polyethylene glycol (18) isostearate, polyethylene glycol (19) isostearate, polyethylene glycol (20) isostearate, polyethylene glycol (21) isostearate, polyethylene glycol (22) isostearate, polyethylene glycol (23) isostearate, polyethylene glycol (24) isostearate, polyethylene glycol (25) isostearate, polyethylene glycol (12) oleate, polyethylene glycol (13) oleate, polyethylene glycol (14) oleate, polyethylene glycol (15) oleate, polyethylene glycol (16) oleate, polyethylene glycol (17) oleate, polyethylene glycol (18) oleate, polyethylene glycol (19) oleate, polyethylene glycol (20) oleate, An ethoxylated alkyl ether carboxylic acid or salt thereof which can advantageously be used is sodium laureth-11 carboxylate. An alkyl ether sulfate which can advantageously be used is sodium laureth-14 sulfate. An ethoxylated cholesterol derivative which can advantageously be used is polyethylene glycol (30) cholesteryl ether. Polyethylene glycol (25) soyasterol has also proven successful. Ethoxylated triglycerides which can advantageously be used are the polyethylene glycol (60) evening primrose glycerides.

It is furthermore advantageous to select the polyethylene glycol glycerol fatty acid esters from the group polyethylene glycol (20) glyceryl laurate, polyethylene glycol (21) glyceryl laurate, polyethylene glycol (22) glyceryl laurate, polyethylene glycol (23) glyceryl laurate, polyethylene glycol (6) glyceryl caprate/caprinate, polyethylene glycol (20) glyceryl oleate, polyethylene glycol (20) glyceryl isostearate, polyethylene glycol (18) glyceryl oleate/cocoate.

It is likewise favourable to select the sorbitan esters from the group polyethylene glycol (20) sorbitan monolaurate, polyethylene glycol (20) sorbitan monostearate, polyethylene glycol (20) sorbitan monoisostearate, polyethylene glycol (20) sorbitan monopalmitate, polyethylene glycol (20) sorbitan monooleate.

Optional W/O emulsifiers, but ones which may nevertheless be advantageously employed in accordance with the invention are the following:
fatty alcohols having 8 to 30 carbon atoms, monoglycerol esters of saturated and/or unsaturated, branched and/or unbranched alkanecarboxylic acids having a chain length of 8 to 24, in particular 12-18 C atoms, diglycerol esters of saturated and/or unsaturated, branched and/or unbranched alkanecarboxylic acids having a chain length of 8 to 24, in particular 12-18 C atoms, monoglycerol ethers of saturated and/or unsaturated, branched and/or unbranched alcohols having a chain length of 8 to 24, in particular 12-18 C atoms, diglycerol ethers of saturated and/or unsaturated, branched and/or unbranched alcohols having a chain length of 8 to 24, in particular 12-18 C atoms, propylene glycol esters of saturated and/or unsaturated, branched and/or unbranched alkanecarboxylic acids having a chain length of 8 to 24, in particular 12-18 C atoms, and sorbitan esters of saturated and/or unsaturated, branched and/or unbranched alkanecarboxylic acids having a chain length of 8 to 24, in particular 12-18 C atoms.

Particularly advantageous W/O emulsifiers are glyceryl monostearate, glyceryl monoisostearate, glyceryl monomyristate, glyceryl monooleate, diglyceryl monostearate, diglyceryl monoisostearate, propylene glycol monostearate, propylene glycol monoisostearate, propylene glycol monocaprylate, propylene glycol monolaurate, sorbitan monoisostearate, sorbitan monolaurate, sorbitan monocaprylate, sorbitan monoisooleate, sucrose distearate, cetyl alcohol, stearyl alcohol, arachidyl alcohol, behenyl alcohol, isobehenyl alcohol, selachyl alcohol, chimyl alcohol, polyethylene glycol (2) stearyl ether (steareth-2), glyceryl monolaurate, glyceryl monocaprinate, glyceryl monocaprylate.

Preferred compositions in accordance with the invention are particularly suitable for protecting human skin against ageing processes and against oxidative stress, i.e. against damage caused by free radicals, as are generated, for example, by solar irradiation, heat or other influences. In this connection, they are in the various administration forms usually used for this application. For example, it may, in particular, be in the form of a lotion or emulsion, such as in the form of a cream or milk (O/W, W/O, O/W/O, W/O/W), in the form of oily-alcoholic, oily-aqueous or aqueous-alcoholic gels or solutions, in the form of solid sticks or may be formulated as an aerosol.

The composition may comprise cosmetic adjuvants which are usually used in this type of composition, such as, for example, thickeners, softeners, moisturisers, surface-active agents, emulsifiers, preservatives, antifoams, perfumes, waxes, lanolin, propellants, dyes and/or pigments which colour the composition itself or the skin, and other ingredients usually used in cosmetics.

The dispersant or solubiliser used can be an oil, wax or other fatty substance, a lower monoalcohol or lower polyol or mixtures thereof. Particularly preferred monoalcohols or polyols include ethanol, isopropanol, propylene glycol, glycerol and sorbitol.

A preferred embodiment of the invention is an emulsion in the form of a protective cream or milk which, apart from the compound(s) according to the invention, comprises, for example, fatty alcohols, fatty acids, fatty acid esters, in particular triglycerides of fatty acids, lanolin, natural and synthetic oils or waxes and emulsifiers in the presence of water.

Further preferred embodiments are oily lotions based on natural or synthetic oils and waxes, lanolin, fatty acid esters, in particular triglycerides of fatty acids, or oily-alcoholic lotions based on a lower alcohol, such as ethanol, or a glycerol, such as propylene glycol, and/or a polyol, such as glycerol, and oils, waxes and fatty acid esters, such as triglycerides of fatty acids.

The composition according to the invention may also be in the form of an alcoholic gel which comprises one or more lower alcohols or polyols, such as ethanol, propylene glycol or glycerol, and a thickener, such as siliceous earth. The oily-alcoholic gels also comprise natural or synthetic oil or wax.

The solid sticks consist of natural or synthetic waxes and oils, fatty alcohols, fatty acids, fatty acid esters, lanolin and other fatty substances.

If a composition is formulated as an aerosol, the customary propellants, such as alkanes, fluoroalkanes and chlorofluoroalkanes, are generally used.

The cosmetic composition may also be used to protect the hair against photochemical damage in order to prevent colour changes, bleaching or damage of a mechanical nature. In this case, a suitable formulation is in the form of a rinse-out shampoo, lotion, gel or emulsion, the composition in question being applied before or after shampooing, before or after colouring or bleaching or before or after permanent waving. It is also possible to select a composition in the form of a lotion or gel for styling and treating the hair, in the form of a lotion or gel for brushing or blow-waving, in the form of a hair lacquer, permanent waving composition, colorant or bleach for the hair. Besides the compound(s) according to the invention, the composition having light-protection properties may comprise various adjuvants used in this type of composition, such as surface-active agents, thickeners, polymers, softeners, preservatives, foam stabilisers, electrolytes, organic solvents, silicone derivatives, oils, waxes, antigrease agents, dyes and/or pigments which colour the composition itself or the hair, or other ingredients usually used for hair care.

If the composition according to the invention is a hair-care composition, it is preferred for this composition to comprise at least one compound of the formula I in which $R^1$ stands for a radical $R^a$ or $R^b$

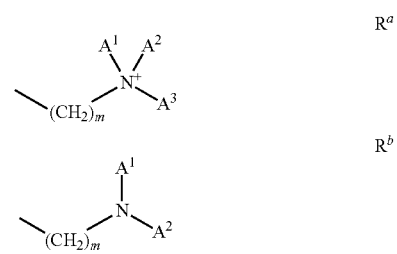

where m stands for an integer from the range from 1 to 3, and $A^1$-$A^3$ each, independently of one another, stand for a radical $-(CH_2)_o(O)_pH$, where o stands for 1, 2 or 3, and p stands for 0 or 1, where it is very particularly preferred for the at least one compound of the formula I to be a compound selected from compounds Iah and Ib to Iv, as described above.

The present invention furthermore relates to a process for the preparation of a composition which is characterised in that at least one compound which does not itself exhibit significant UV absorption in the UV-A or UV-B region, but is reactive under use conditions and develops UV-A or UV-B protection, is mixed with a vehicle which is suitable cosmetically or dermatologically or for foods or for domestic products, and to the use of a compound of the formula I for the preparation of a composition having antioxidant properties.

The compositions according to the invention can be prepared with the aid of techniques which are well known to the person skilled in the art.

The mixing can result in dissolution, emulsification or dispersion of the compound according to the invention in the vehicle.

In a process which is preferred in accordance with the invention, the compound of the formula I is prepared by hydrogenation of at least one compound of the formula I ena or I enb

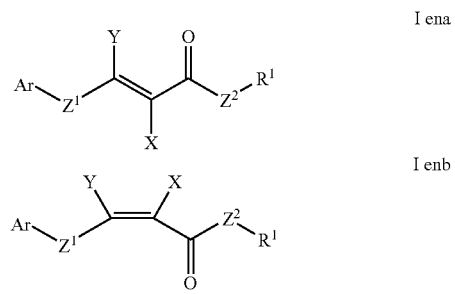

where the radicals Ar, X, Y, $Z^1$ and $Z^2$ and $R^1$ correspond to those of the desired formula I.

Molecular hydrogen, for example, is suitable for the hydrogenation. If molecular hydrogen is used for the hydrogenation of the compounds of the formula I ena or I enb, the hydrogenation is preferably carried out in the presence of a catalyst or catalyst system.

Suitable catalysts for the hydrogenation are all common homogeneous and heterogeneous catalysts, particularly preferably at least one noble metal, preferably selected from the elements Pt, Pd and Rh, or a transition metal, such as Mo, W, Cr, but particularly Fe, Co and Ni, either individually or in a mixture. The catalyst(s) or catalyst mixture(s) here may also be employed on supports, such as carbon, activated carbon, aluminium oxide, barium carbonate, barium sulfate, calcium carbonate, strontium carbonate or kieselguhr. The metal here may also be employed in the form of the Raney compound, for example Raney nickel. If the catalysis is carried out in a homogeneous process, it is preferred for the catalyst employed to be one or more complex compounds of the said metals, such as, for example, Wilkinson's catalyst [chlorotris (triphenylphosphine)rhodium]. It is furthermore possible to employ salts of the said metals, which can be reduced in situ by a reducing agent and form a finely divided metal(0) species in situ. Suitable noble-metal salts are, for example, palladium acetate, palladium bromide and palladium chloride, suitable reducing agents are, for example, hydrogen, hydrazine, sodium borohydride and formates. In a preferred variant of the present invention, a heterogeneous catalyst is employed, it being particularly preferred for the catalyst employed in the process according to the invention to be Pd or Pt, preferably on activated-carbon support, for example 5% by weight of Pd or Pt on C.

The hydrogenation is usually carried out at a temperature in the range from 20-150° C. The hydrogenation is furthermore advantageously carried out at a hydrogen pressure of 1 to 200 bar.

Suitable solvents are protic solvents, in particular the usual protic solvents known to the person skilled in the art, such as water, lower alcohols, such as, for example, methanol, ethanol and isopropanol, and primary and secondary amines, and mixtures of protic solvents of this type, where it may be particularly preferred for the solvent employed to be water.

Suitable solvents for this reaction are furthermore also conventional aprotic solvents. For example, diethyl ether, tetrahydrofuran, benzene, toluene, acetonitrile, dimethoxyethane, dimethylformamide, dimethyl sulfoxide and N-methylpyrrolidone can be employed.

In a likewise preferred embodiment of the preparation process according to the invention, the hydrogenation is carried out in the solid state, i.e. no additional solvent is necessary.

When the reaction is complete, the work-up can be carried out by conventional methods. For example, the catalyst can be filtered off, the filtrate freed from solvent, for example by heating at reduced pressure compared with atmospheric pressure, and the resultant product purified further by conventional methods.

The further purification of the reaction products can likewise be carried out by conventional methods, for example by recrystallisation from a suitable solvent, or by chromatographic methods.

It has also been noted that compounds according to the invention can have a stabilising effect on the composition. When used in corresponding products, the latter thus also remain stable for longer and do not change their pharmaceutical and sensory nature. In particular, the effectiveness of the ingredients, for example vitamins, is retained even in the case of application over extended periods or extended storage. This is, inter alia, particularly advantageous in the case of compositions for protecting the skin against the effect of UV rays since these cosmetics are exposed to particularly high stresses by UV radiation.

The positive effects of compounds according to the invention give rise to their particular suitability for use in cosmetic or pharmaceutical compositions.

The properties of compounds of the formula I should likewise be regarded as positive for use in foods or as food supplements or as functional foods. The further explanations given for foods also apply correspondingly to food supplements and functional foods.

The foods which can be enriched with one or more compounds according to the invention in accordance with the present invention include all materials which are suitable for consumption by animals or consumption by humans, for example vitamins and provitamins thereof, fats, minerals or amino acids. (The foods may be solid, but also liquid, i.e. in the form of a beverage).

The present invention accordingly furthermore relates to the use of a compound of the formula I as food additive for human or animal nutrition, and to compositions which are foods or food supplements and comprise corresponding vehicles.

Foods which can be enriched with one or more compounds according to the invention in accordance with the present invention are, for example, also foods which originate from a single natural source, such as, for example, sugar, unsweetened juice, squash or puree of a single plant species, such as, for example, unsweetened apple juice (for example also a mixture of different types of apple juice), grapefruit juice, orange juice, apple compote, apricot squash, tomato juice, tomato sauce, tomato puree, etc. Further examples of foods which can be enriched with one or more compounds according to the invention in accordance with the present invention are corn or cereals from a single plant species and materials produced from plant species of this type, such as, for example, cereal syrup, rye flour, wheat flour or oat bran. Mixtures of foods of this type are also suitable for being enriched with one or more compounds according to the invention in accordance with the present invention, for example multivitamin preparations, mineral mixtures or sweetened juice. As further examples of foods which can be enriched with one or more compounds according to the invention in accordance with the present invention, mention may be made of food compositions, for example prepared cereals, biscuits, mixed drinks, foods prepared especially for children, such as yoghurt, diet foods, low-calorie foods or animal feeds.

The foods which can be enriched with one or more compounds according to the invention in accordance with the present invention thus include all edible combinations of carbohydrates, lipids, proteins, inorganic elements, trace elements, vitamins, water or active metabolites of plants and animals.

The foods which can be enriched with one or more compounds according to the invention in accordance with the present invention are preferably administered orally, for example in the form of meals, pills, tablets, capsules, powders, syrup, solutions or suspensions.

The foods according to the invention enriched with one or more compounds according to the invention can be prepared with the aid of techniques which are well known to the person skilled in the art.

Due to their action as antioxidants or free-radical scavengers, compounds according to the invention are also suitable as medicament ingredient, where they support or replace natural mechanisms which scavenge free radicals in the body. The compounds according to the invention can in some cases be compared in their action with free-radical scavengers, such as vitamin C. Compounds according to the invention can be used, for example, for the preventative treatment of inflammation and allergies of the skin and in certain cases for preventing certain types of cancer. Compounds according to the invention are particularly suitable for the preparation of a medicament for the treatment of inflammation, allergies and irritation, in particular of the skin. It is furthermore possible to prepare medicaments which act as vein tonic, as agent for increasing the strength of blood capillaries, as cuperose inhibitor, as inhibitor of chemical, physical or actinic erythemas, as agent for the treatment of sensitive skin, as decongestant, as dehydration agent, as slimming agent, as anti-wrinkle agent, as stimulators of the synthesis of components of the extracellular matrix, as strengthening agent for improving skin elasticity, and as anti-ageing agent. Furthermore, compounds according to the invention which are preferred in this connection exhibit anti-allergic and anti-inflammatory and anti-irritative actions. They are therefore suitable for the preparation of medicaments for the treatment of inflammation or allergic reactions.

The invention is explained in greater detail below with reference to examples. The invention can be carried out throughout the scope claimed and is not restricted to the examples given here.

EXAMPLES

Example 1

Preparation of di-2-ethylhexyl 4-hydroxy-3,5-dimethoxybenzylmalonate

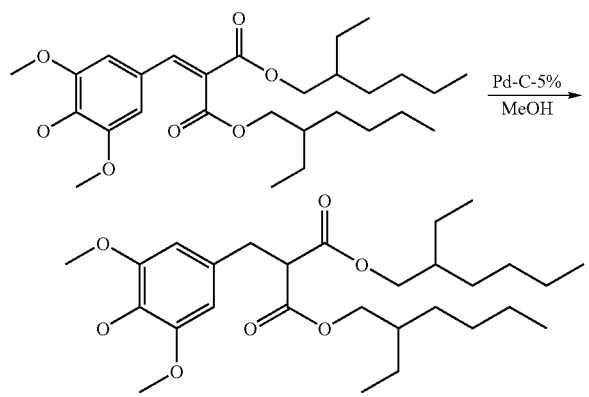

Di-2-ethylhexyl(4-hydroxy-3,5-dimethoxybenzylidene) malonate (the synthesis of this compound is described in WO-A-2003/007906, the disclosure content of which in this respect is expressly part of the subject-matter of the present application) is dissolved in methanol (14 ml/mmol), and 5% Pd/C (56% water; Merck: Art. No. 275175; 0.54 g/mmol) is added. The hydrogenation is subsequently carried out with hydrogen 3.0 at room temperature and atmospheric pressure. The catalyst is separated off by filtration. The filtrate is freed from solvent in vacuo, and the greenish oil remaining is taken up in tert-butyl methyl ether (MTBE) and extracted 2× with 1 N HCl, 1× with saturated, aqueous NaHCO₃ solution and 1× with saturated, aqueous NaCl solution. The organic phase is dried over sodium sulfate, and the solvent is removed in vacuo. The purification is carried out by filtration through silica gel. To this end, the crude product is taken up in petroleum ether (PE) and eluted with PE/MTBE, giving analytically pure product as colourless oil.

Example 2

Preparation of 2-ethylhexyl 2-cyano-3,3,-diphenyl-propionate

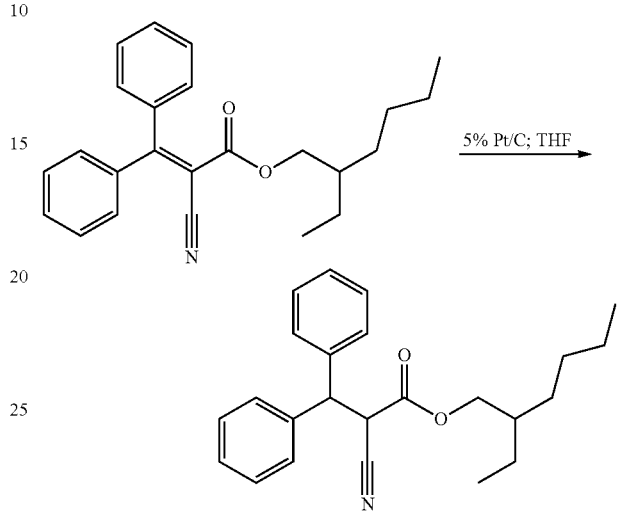

2-Ethylhexyl 2-cyano-3,3-diphenylacrylate (Eusolex® OCR; Merck) is dissolved in tetrahydrofuran (THF), and 5% Pd/C (56% water; Merck: Art. No. 275175) is added. The hydrogenation is subsequently carried out with hydrogen 3.0 at room temperature and atmospheric pressure. The catalyst is separated off by filtration. The filtrate is freed from solvent in vacuo, and the residue is washed. The organic phase is dried over sodium sulfate, and the solvent is removed in vacuo. The purification is carried out by filtration through silica gel, giving analytically pure product.

In principle, all compounds of the formula I can be prepared analogously to Example 1 or 2. For example, the following compounds can be obtained from the respective corresponding benzylidene compounds:

di-2-ethylhexyl 4-methoxybenzylmalonate,
2-ethylhexyl 4-methoxyphenylpropionate,
2-ethylhexyl 4-hydroxy-3,5-dimethoxyphenylpropionate,
diethyl 4-hydroxy-3,5-dimethoxybenzylmalonate,
2-ethylhexyl 4-hydroxyphenylpropionate,
di-2-ethylhexyl 4-hydroxybenzylmalonate,
2-ethylhexyl 3-hydroxyphenylpropionate,
di-2-ethylhexyl 3-hydroxybenzylmalonate,
2-ethylhexyl 2-hydroxyphenylpropionate,
di-2-ethylhexyl 2-hydroxybenzylmalonate,
di-2-ethylhexyl 3,4,5-trimethoxybenzylmalonate,
2-ethylhexyl 3,4,5-trimethoxyphenylpropionate,
di-2-ethylhexyl 2,4,5-trimethoxybenzylmalonate,
2-ethylhexyl 2,4,5-trimethoxyphenylpropionate,
di-2-ethylhexyl 2,3,4-trimethoxybenzylmalonate,
2-ethylhexyl 2,3,4-trimethoxyphenylpropionate,
di-2-ethylhexyl 2,3,5-trimethoxybenzylmalonate,
2-ethylhexyl 2,3,5-trimethoxyphenylpropionate,
di-2-ethylhexyl 2,3,6-trimethoxybenzylmalonate,
2-ethylhexyl 2,3,6-trimethoxyphenylpropionate,
di-2-ethylhexyl 2,4,6-trimethoxybenzylmalonate,
2-ethylhexyl 2,4,6-trimethoxyphenylpropionate,
di-2-ethylhexyl 2,4-dimethoxybenzylmalonate, 2-ethylhexyl 2,4-dimethoxyphenylpropionate,
di-2-ethylhexyl 2,3-dimethoxybenzylmalonate,
2-ethylhexyl 2,3-dimethoxyphenylpropionate,
di-2-ethylhexyl 2,5-dimethoxybenzylmalonate,
2-ethylhexyl 2,5-dimethoxyphenylpropionate,
di-2-ethylhexyl 3,4-dimethoxybenzylmalonate,
2-ethylhexyl 3,4-dimethoxyphenylpropionate,
di-2-ethylhexyl 3,5-dimethoxybenzylmalonate,
2-ethylhexyl 3,5-dimethoxyphenylpropionate,
2-ethylhexyl 4-hydroxy-3-methoxyphenylpropionate,
di-2-ethylhexyl 4-hydroxy-3-methoxybenzylmalonate,
di-2-ethylhexyl 3,4,5-trihydroxybenzylmalonate,
2-ethylhexyl 3,4,5-trihydroxyphenylpropionate,
di-2-ethylhexyl 2,4,5-trihydroxybenzylmalonate,
2-ethylhexyl 2,4,5-trihydroxyphenylpropionate,
di-2-ethylhexyl 2,3,4-trihydroxybenzylmalonate,
2-ethylhexyl 2,3,4-trihydroxyphenylpropionate,
di-2-ethylhexyl 2,4-dihydroxybenzylmalonate,
2-ethylhexyl 2,4-dihydroxyphenylpropionate,
di-2-ethylhexyl 2,3-dihydroxybenzylmalonate,
2-ethylhexyl 2,3-dihydroxyphenylpropionate,
di-2-ethylhexyl 2,5-dihydroxybenzylmalonate,
2-ethylhexyl 2,5-dihydroxyphenylpropionate,
di-2-ethylhexyl 3,4-dihydroxybenzylmalonate,
2-ethylhexyl 3,4-dihydroxyphenylpropionate,
di-2-ethylhexyl 3,5-dihydroxybenzylmalonate,
2-ethylhexyl 3,5-dihydroxyphenylpropionate,
2-ethylhexyl 3-hydroxy-4-methoxyphenylpropionate,
di-2-ethylhexyl 3-hydroxy-4-methoxybenzylmalonate,
4-methoxybenzylmalonic acid,
4-methoxyphenylpropionic acid,
4-hydroxy-3,5-dimethoxyphenylpropionic acid,
4-hydroxyphenylpropionic acid,
4-hydroxybenzylmalonic acid,
3-hydroxyphenylpropionic acid,
3-hydroxybenzylmalonic acid,
2-hydroxyphenylpropionic acid,
2-hydroxybenzylmalonic acid,
3,4,5-trimethoxybenzylmalonic acid,
3,4,5-trimethoxyphenylpropionic acid,
2,4,5-trimethoxybenzylmalonic acid,
2,4,5-trimethoxyphenylpropionic acid,
2,3,4-trimethoxybenzylmalonic acid,
2,3,4-trimethoxyphenylpropionic acid,
2,3,5-trimethoxybenzylmalonic acid,
2,3,5-trimethoxyphenylpropionic acid,
2,3,6-trimethoxybenzylmalonic acid,
2,3,6-trimethoxyphenylpropionic acid,
2,4,6-trimethoxybenzylmalonic acid,
2,4,6-trimethoxyphenylpropionic acid,
2,4-dimethoxybenzylmalonic acid,
2,4-dimethoxyphenylpropionic acid,
2,3-dimethoxybenzylmalonic acid,
2,3-dimethoxyphenylpropionic acid,
2,5-dimethoxybenzylmalonic acid,
2,5-dimethoxyphenylpropionic acid,
3,4-dimethoxybenzylmalonic acid,
3,4-dimethoxyphenylpropionic acid,
3,5-dimethoxybenzylmalonic acid,
3,5-dimethoxyphenylpropionic acid,
4-hydroxy-3-methoxyphenylpropionic acid,
4-hydroxy-3-methoxybenzylmalonic acid,
3,4,5-trihydroxybenzylmalonic acid,
3,4,5-trihydroxyphenylpropionic acid,
2,4,5-trihydroxybenzylmalonic acid,
2,4,5-trihydroxyphenylpropionic acid,
2,3,4-trihydroxybenzylmalonic acid,
2,3,4-trihydroxyphenylpropionic acid,
2,4-dihydroxybenzylmalonic acid,
2,4-dihydroxyphenylpropionic acid,
2,3-dihydroxybenzylmalonic acid,
2,3-dihydroxyphenylpropionic acid,
2,5-dihydroxybenzylmalonic acid,
2,5-dihydroxyphenylpropionic acid,
3,4-dihydroxybenzylmalonic acid,
3,4-dihydroxyphenylpropionic acid,
3,5-dihydroxybenzylmalonic acid,
3,5-dihydroxyphenylpropionic acid,
3-hydroxy-4-methoxyphenylpropionic acid,
3-hydroxy-4-methoxybenzylmalonic acid,
diethyl 4-methoxybenzylmalonate,
ethyl 4-methoxyphenylpropionate,
ethyl 4-hydroxy-3,5-dimethoxyphenylpropionate,
diethyl 3,4,5-trimethoxybenzylmalonate,
ethyl 3,4,5-trimethoxyphenylpropionate,
diethyl 2,4,5-trimethoxybenzylmalonate,
ethyl 2,4,5-trimethoxyphenylpropionate,
diethyl 2,3,4-trimethoxybenzylmalonate,
ethyl 2,3,4-trimethoxyphenylpropionate,
diethyl 2,3,5-trimethoxybenzylmalonate,
ethyl 2,3,5-trimethoxyphenylpropionate,
diethyl 2,3,6-trimethoxybenzylmalonate,
ethyl 2,3,6-trimethoxyphenylpropionate,
diethyl 2,4,6-trimethoxybenzylmalonate,
ethyl 2,4,6-trimethoxyphenylpropionate,
diethyl 2,4-dimethoxybenzylmalonate,
ethyl 2,4-dimethoxyphenylpropionate,
diethyl 2,3-dimethoxybenzylmalonate,
ethyl 2,3-dimethoxyphenylpropionate,
diethyl 2,5-dimethoxybenzylmalonate,
ethyl 2,5-dimethoxyphenylpropionate,
diethyl 3,4-dimethoxybenzylmalonate,
ethyl 3,4-dimethoxyphenylpropionate,
diethyl 3,5-dimethoxybenzylmalonate,
ethyl 3,5-dimethoxyphenylpropionate,
ethyl 4-hydroxy-3-methoxyphenylpropionate,
diethyl 4-hydroxy-3-methoxybenzylmalonate,
diethyl 3,4,5-trihydroxybenzylmalonate,
ethyl 3,4,5-trihydroxyphenylpropionate,
diethyl 2,4,5-trihydroxybenzylmalonate,
ethyl 2,4,5-trihydroxyphenylpropionate,
diethyl 2,3,4-trihydroxybenzylmalonate,
ethyl 2,3,4-trihydroxyphenylpropionate,
diethyl 2,4-dihydroxybenzylmalonate,
ethyl 2,4-dihydroxyphenylpropionate,
diethyl 2,3-dihydroxybenzylmalonate,
ethyl 2,3-dihydroxyphenylpropionate,
diethyl 2,5-dihydroxybenzylmalonate,
ethyl 2,5-dihydroxyphenylpropionate,
diethyl 3,4-dihydroxybenzylmalonate,
ethyl 3,4-dihydroxyphenylpropionate,
diethyl 3,5-dihydroxybenzylmalonate,
ethyl 3,5-dihydroxyphenylpropionate,
ethyl 3-hydroxy-4-methoxyphenylpropionate,
diethyl 3-hydroxy-4-methoxybenzylmalonate,
diphenethyl 4-methoxybenzylmalonate,
phenethyl 4-methoxyphenylpropionate,
phenethyl 4-hydroxy-3,5-dimethoxyphenylpropionate,
diphenethyl 3,4,5-trimethoxybenzylmalonate,
phenethyl 3,4,5-trimethoxyphenylpropionate,
diphenethyl 2,4,5-trimethoxybenzylmalonate,
phenethyl 2,4,5-trimethoxyphenylpropionate,
diphenethyl 2,3,4-trimethoxybenzylmalonate,
phenethyl 2,3,4-trimethoxyphenylpropionate, diphenethyl 2,3,5-trimethoxybenzylmalonate,
phenethyl 2,3,5-trimethoxyphenylpropionate,
diphenethyl 2,3,6-trimethoxybenzylmalonate,
phenethyl 2,3,6-trimethoxyphenylpropionate,
diphenethyl 2,4,6-trimethoxybenzylmalonate,
phenethyl 2,4,6-trimethoxyphenylpropionate,
diphenethyl 2,4-dimethoxybenzylmalonate,
phenethyl 2,4-dimethoxyphenylpropionate,
diphenethyl 2,3-dimethoxybenzylmalonate,
phenethyl 2,3-dimethoxyphenylpropionate,
diphenethyl 2,5-dimethoxybenzylmalonate,
phenethyl 2,5-dimethoxyphenylpropionate,
diphenethyl 3,4-dimethoxybenzylmalonate,
phenethyl 3,4-dimethoxyphenylpropionate,
diphenethyl 3,5-dimethoxybenzylmalonate,
phenethyl 3,5-dimethoxyphenylpropionate,
phenethyl 4-hydroxy-3-methoxyphenylpropionate,
diphenethyl 4-hydroxy-3-methoxybenzylmalonate,
diphenethyl 3,4,5-trihydroxybenzylmalonate,
phenethyl 3,4,5-trihydroxyphenylpropionate,
diphenethyl 2,4,5-trihydroxybenzylmalonate,
phenethyl 2,4,5-trihydroxyphenylpropionate,
diphenethyl 2,3,4-trihydroxybenzylmalonate,
phenethyl 2,3,4-trihydroxyphenylpropionate,
diphenethyl 2,4-dihydroxybenzylmalonate,
phenethyl 2,4-dihydroxyphenylpropionate,
diphenethyl 2,3-dihydroxybenzylmalonate,
phenethyl 2,3-dihydroxyphenylpropionate,
diphenethyl 2,5-dihydroxybenzylmalonate,
phenethyl 2,5-dihydroxyphenylpropionate,
diphenethyl 3,4-dihydroxybenzylmalonate,
phenethyl 3,4-dihydroxyphenylpropionate,
diphenethyl 3,5-dihydroxybenzylmalonate,
phenethyl 3,5-dihydroxyphenylpropionate,
phenethyl 3-hydroxy-4-methoxyphenylpropionate,
diphenethyl 3-hydroxy-4-methoxybenzylmalonate,
ethyl 2-cyano-3,3-diphenylpropionate,
2-ethylhexyl 2-cyano-3,3-diphenylpropionate,
2-cyano-3,3-diphenylpropionic acid,
chloride of N,N'-bis[3-(ethyldimethylammonium)propyl]-2-(4-hydroxy-3,5-dimethoxybenzyl)malonamide,
chloride of N,N'-bis[3-(ethyldimethylammonium)ethyl]-2-(4-hydroxy-3,5-dimethoxybenzyl)malonamide,
chloride of N,N'-bis[3-(trimethylammonium)propyl]-2-(4-hydroxy-3,5-dimethoxybenzyl)malonamide,
chloride of N,N'-bis[3-(trimethylammonium)ethyl]-2-(4-hydroxy-3,5-dimethoxybenzyl)malonamide,
chloride of N,N'-bis[3-(ethyldimethylammonium)propyl]-2-(4-hydroxy-3-methoxybenzyl)malonamide,
chloride of N,N'-bis[3-(ethyldimethylammonium)ethyl]-2-(4-hydroxy-3-methoxybenzyl)malonamide,
chloride of N,N'-bis[3-(trimethylammonium)propyl]-2-(4-hydroxy-3-methoxybenzyl)malonamide,
chloride of N,N'-bis[3-(trimethylammonium)ethyl]-2-(4-hydroxy-3-methoxybenzyl)malonamide,
oligo- and polysiloxanes which contain benzylmalonic acid derivatives or phenylpropionic acid derivatives bonded via alkyleneoxy functions, such as, for example, diethyl 4-alkyleneoxybenzylmalonate.

Example 3

Oxidation in UV Light

FIG. 1 shows the change in the UV spectrum of di-2-ethylhexyl 4-hydroxy-3,5-dimethoxybenzylmalonate (from Example 1) on irradiation with UV light.

The curves stand for the unirradiated substance (exposed to 0 kJ/m$^2$), after irradiation for 15 min (exposure to 86 kJ/m$^2$), after irradiation for 65 min (exposure to 373 kJ/m$^2$), after irradiation for 235 min (exposure to 1349 kJ/m$^2$) and after irradiation for 405 min (exposure to 2325 kJ/m$^2$). The spectra are recorded on a Carry 300 bio spectrometer. The irradiation is carried out by means of an Atlas Sun Test CPS, xenon lamp with UV special-glass filter at a power of 95.69 W/m$^2$ in the range 290-400 nm.

After only 65 min, a significantly increased UV absorption by the compound in the UV-A region ($E_{max}$ in the range 320-340 nm), which increases further on longer irradiation, is evident.

Example 3a

Oxidation in UV Light in the Presence of Further Antioxidants

Figure 2:
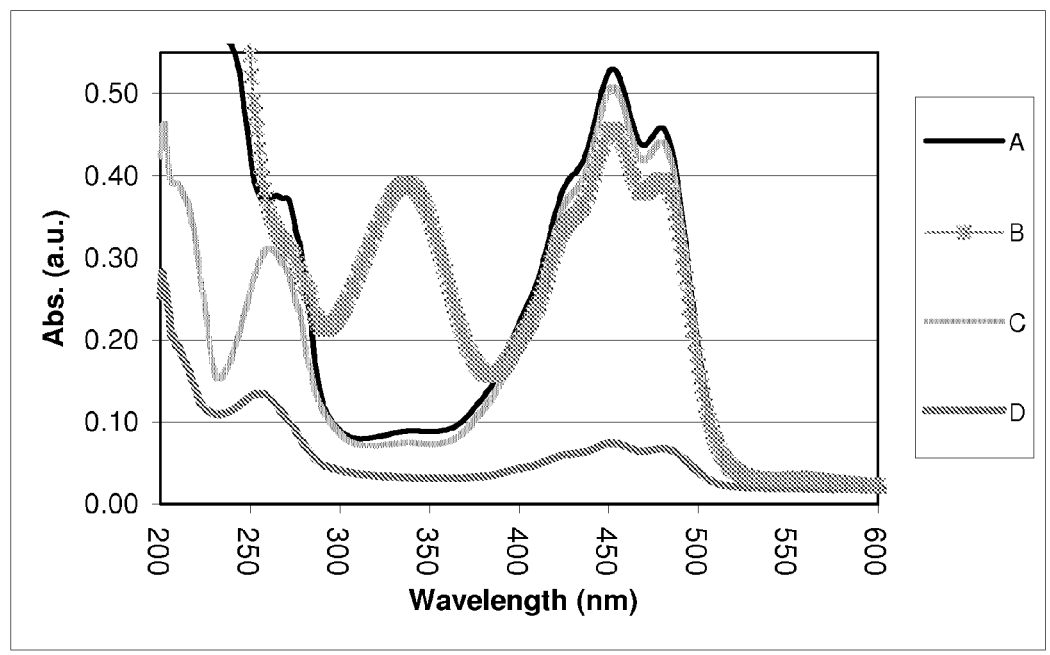

FIG. 2 shows the change in the UV/VIS spectrum of emulsions comprising 0.5% by weight of beta-carotene and 4% by weight of di-2-ethylhexyl 4-hydroxy-3,5-dimethoxybenzylmalonate (curves A and B) compared with an emulsion comprising 0.5% by weight of beta-carotene, but no di-2-ethylhexyl 4-hydroxy-3,5-dimethoxybenzylmalonate (curves C and D) on irradiation with UV light (cf. Example 3).

The curves stand for the unirradiated emulsions (curves A and C) and the emulsions after irradiation for 90 min (curves B and D). The spectra are recorded on a Carry 50 spectrometer. The irradiation is carried out by means of an Atlas Sun Test CPS$^+$ xenon lamp with UV special-glass filter. The results are from 4-fold determinations (n=4).

For the irradiated sample (B) comprising di-2-ethylheyl 4-hydroxy-3,5-dimethoxybenzylmalonate, the absorption of the reaction product in the UV-A region ($E_{max}$ in the range 320-340 nm) is again evident. In addition, however, it can be seen that the absorption of the beta-carotene ($E_{max}$ in the range 440-480 nm) in this sample is significantly stronger compared with the irradiated sample D. Consequently, beta-carotene degradation in the emulsion according to the invention is reduced; di-2-ethylhexyl 4-hydroxy-3,5-dimethoxybenzylmalonate stabilises the beta-carotene.

Example 4

Compositions

Illustrative formulations of cosmetic compositions which comprise compounds according to Example 1 or 2 are indicated below. Corresponding compositions can be prepared in the same way with all compounds according to the invention.

In addition, the INCI names of the commercially available compounds are indicated.

UV-Pearl, OMC stands for the composition having the INCI name: Water (for EU: Aqua), Ethylhexyl Methoxycinnamate, Silica, PVP, Chlorphenesin, BHT; this composition is commercially available from Merck KGaA, Darmstadt, under the name Eusolex®UV Pearl™OMC.

The other UV-Pearls indicated in the tables each have an analogous composition, with OMC being replaced by the UV filters indicated.

TABLE 1

| W/O emulsions (numbers in % by weight) | | | | | | | | | | |
|---|---|---|---|---|---|---|---|---|---|---|
| | 1-1 | 1-2 | 1-3 | 1-4 | 1-5 | 1-6 | 1-7 | 1-8 | 1-9 | 1-10 |
| Titanium Dioxide | | 2 | 5 | | | | | | | 3 |
| Di-2-ethylhexyl 4-hydroxy-3,5-dimethoxybenzyl-malonate | 5 | 3 | 2 | 1 | 2 | 1 | 2 | 1 | 1 | 1 |
| Zinc Oxide | | | | | | | | 5 | 2 | |
| UV-Pearl, OMC | 30 | 15 | 15 | 15 | 15 | 15 | 15 | 15 | 15 | 15 |
| Polyglyceryl 3-Dimerate | 3 | 3 | 3 | 3 | 3 | 3 | 3 | 3 | 3 | 3 |
| Cera Alba | 0.3 | 0.3 | 0.3 | 0.3 | 0.3 | 0.3 | 0.3 | 0.3 | 0.3 | 0.3 |
| Hydrogenated Castor Oil | 0.2 | 0.2 | 0.2 | 0.2 | 0.2 | 0.2 | 0.2 | 0.2 | 0.2 | 0.2 |
| Paraffinium Liquidum | 7 | 7 | 7 | 7 | 7 | 7 | 7 | 7 | 7 | 7 |
| Caprylic/Capric Triglyceride | 7 | 7 | 7 | 7 | 7 | 7 | 7 | 7 | 7 | 7 |
| Hexyl Laurate | 4 | 4 | 4 | 4 | 4 | 4 | 4 | 4 | 4 | 4 |
| PVP/Eicosene Copolymer | 2 | 2 | 2 | 2 | 2 | 2 | 2 | 2 | 2 | 2 |
| Propylene Glycol | 4 | 4 | 4 | 4 | 4 | 4 | 4 | 4 | 4 | 4 |
| Magnesium Sulfate | 0.6 | 0.6 | 0.6 | 0.6 | 0.6 | 0.6 | 0.6 | 0.6 | 0.6 | 0.6 |
| Tocopherol | 0.5 | 0.5 | 0.5 | 0.5 | 0.5 | 0.5 | 0.5 | 0.5 | 0.5 | 0.5 |
| Tocopheryl Acetate | 0.5 | 0.5 | 0.5 | 0.5 | 0.5 | 0.5 | 0.5 | 0.5 | 0.5 | 0.5 |
| Cyclomethicone | 0.5 | 0.5 | 0.5 | 0.5 | 0.5 | 0.5 | 0.5 | 0.5 | 0.5 | 0.5 |
| Propylparaben | 0.05 | 0.05 | 0.05 | 0.05 | 0.05 | 0.05 | 0.05 | 0.05 | 0.05 | 0.05 |
| Methylparaben | 0.15 | 0.15 | 0.15 | 0.15 | 0.15 | 0.15 | 0.15 | 0.15 | 0.15 | 0.15 |
| Water | to 100 | to 100 | to 100 | to 100 | to 100 | to 100 | to 100 | to 100 | to 100 | to 100 |

| | 1-11 | 1-12 | 1-13 | 1-14 | 1-15 | 1-16 | 1-17 | 1-18 |
|---|---|---|---|---|---|---|---|---|
| Titanium Dioxide | 3 | | 2 | | 3 | | 2 | 5 |
| Benzylidene Malonate Polysiloxane | | 1 | 0.5 | | | | | |
| 2-Ethylhexyl 4-hydroxyphenyl-propionate | 1 | 1 | 0.5 | | | | | |
| Di-2-ethylhexyl 4-hydroxy-3,5-dimethoxybenzylmalonate | 5 | 3 | 2 | 5 | 1 | 3 | 7 | 2 |
| Polyglyceryl 3-Dimerate | 3 | 3 | 3 | 3 | | | | |
| Cera Alba | 0.3 | 0.3 | 0.3 | 0.3 | 2 | 2 | 2 | 2 |
| Hydrogenated Castor Oil | 0.2 | 0.2 | 0.2 | 0.2 | | | | |
| Paraffinium Liquidum | 7 | 7 | 7 | 7 | | | | |
| Caprylic/Capric Triglyceride | 7 | 7 | 7 | 7 | | | | |
| Hexyl Laurate | 4 | 4 | 4 | 4 | | | | |
| PVP/Eicosene Copolymer | 2 | 2 | 2 | 2 | | | | |
| Propylene Glycol | 4 | 4 | 4 | 4 | | | | |
| Magnesium Sulfate | 0.6 | 0.6 | 0.6 | 0.6 | | | | |
| Tocopherol | 0.5 | 0.5 | 0.5 | 0.5 | | | | |
| Tocopheryl Acetate | 0.5 | 0.5 | 0.5 | 0.5 | 1 | 1 | 1 | 1 |
| Cyclomethicone | 0.5 | 0.5 | 0.5 | 0.5 | | | | |
| Propylparaben | 0.05 | 0.05 | 0.05 | 0.05 | 0.05 | 0.05 | 0.05 | 0.05 |
| Methylparaben | 0.15 | 0.15 | 0.15 | 0.15 | 0.15 | 0.15 | 0.15 | 0.15 |
| Dicocoyl Pentyerythrityl Citrate (and) Sorbitan Sesquioleate (and) Cera Alba (and) Aluminium Stearate | | | | | 6 | 6 | 6 | 6 |
| PEG-7 Hydrogenated Castor Oil | | | | | 1 | 1 | 1 | 1 |
| Zinc Stearate | | | | | 2 | 2 | 2 | 2 |
| Oleyl Erucate | | | | | 6 | 6 | 6 | 6 |
| Decyl Oleate | | | | | 6 | 6 | 6 | 6 |
| Dimethicone | | | | | 5 | 5 | 5 | 5 |
| Tromethamine | | | | | 1 | 1 | 1 | 1 |
| Glycerin | | | | | 5 | 5 | 5 | 5 |
| Allantoin | | | | | 0.2 | 0.2 | 0.2 | 0.2 |
| Water | to 100 | to 100 | to 100 | to 100 | to 100 | to 100 | to 100 | to 100 |

| | 1-19 | 1-20 | 1-21 | 1-22 | 1-23 | 1-24 | 1-25 | 1-26 | 1-27 | 1-28 | 1-29 |
|---|---|---|---|---|---|---|---|---|---|---|---|
| Titanium Dioxide | | 2 | 5 | | | | | | | 3 | 3 |
| Benzylidene Malonate Polysiloxane | | | | 1 | | | | | 1 | 1 | |
| Methylene Bis-Benzotriazolyl Tetramethylbutylphenol | | | | | 1 | 2 | 1 | | | | 1 |
| Zinc Oxide | | | | | | | | 5 | 2 | | |
| 2-Ethylhexyl 4-hydroxyphenyl-propionate | 5 | 5 | 5 | 5 | 7 | 5 | 5 | 5 | 5 | 5 | 8 |
| UV-Pearl, OCR | | 10 | | | | | | | | | 5 |
| UV-Pearl, EthylhexylDimethylPABA | | | 10 | | | | | | | | |
| Di-2-ethylhexyl 4-hydroxy-3,5-dimethoxybenzylmalonate | 2 | 4 | 5 | 6 | 3 | 1 | 6 | 10 | 1 | 2 | 5 |
| UV-Pearl, Homosalate, BP-3 | | | | | | | | | 10 | | |
| UV-Pearl, Ethylhexyl Salicylate, BP-3 | | | | | | | | | | 10 | |
| BMDBM | | | | | | | | | | | 2 |

TABLE 1-continued

W/O emulsions (numbers in % by weight)

| | | | | | | | | | | | |
|---|---|---|---|---|---|---|---|---|---|---|---|
| UV-Pearl OMC, | 25 | | | | | | | | | | |
| 4-Methylbenzylidene Camphor | | | | | | | | | | | |
| Polyglyceryl 3-Dimerate | 3 | 3 | 3 | 3 | 3 | 3 | 3 | 3 | 3 | 3 | 3 |
| Cera Alba | 0.3 | 0.3 | 0.3 | 0.3 | 0.3 | 0.3 | 0.3 | 0.3 | 0.3 | 0.3 | 0.3 |
| Hydrogenated Castor Oil | 0.2 | 0.2 | 0.2 | 0.2 | 0.2 | 0.2 | 0.2 | 0.2 | 0.2 | 0.2 | 0.2 |
| Paraffinium Liquidum | 7 | 7 | 7 | 7 | 7 | 7 | 7 | 7 | 7 | 7 | 7 |
| Caprylic/Capric Triglyceride | 7 | 7 | 7 | 7 | 7 | 7 | 7 | 7 | 7 | 7 | 7 |
| Hexyl Laurate | 4 | 4 | 4 | 4 | 4 | 4 | 4 | 4 | 4 | 4 | 4 |
| PVP/Eicosene Copolymer | 2 | 2 | 2 | 2 | 2 | 2 | 2 | 2 | 2 | 2 | 2 |
| Propylene Glycol | 4 | 4 | 4 | 4 | 4 | 4 | 4 | 4 | 4 | 4 | 4 |
| Magnesium Sulfate | 0.6 | 0.6 | 0.6 | 0.6 | 0.6 | 0.6 | 0.6 | 0.6 | 0.6 | 0.6 | 0.6 |
| Tocopherol | 0.5 | 0.5 | 0.5 | 0.5 | 0.5 | 0.5 | 0.5 | 0.5 | 0.5 | 0.5 | 0.5 |
| Tocopheryl Acetate | 0.5 | 0.5 | 0.5 | 0.5 | 0.5 | 0.5 | 0.5 | 0.5 | 0.5 | 0.5 | 0.5 |
| Phenethyl 3,4-dihydroxyphenyl-propionate | 0.5 | 0.5 | 0.5 | 0.5 | 0.5 | 0.5 | 0.5 | 0.5 | 0.5 | 0.5 | 0.5 |
| Propylparaben | 0.05 | 0.05 | 0.05 | 0.05 | 0.05 | 0.05 | 0.05 | 0.05 | 0.05 | 0.05 | 0.05 |
| Methylparaben | 0.15 | 0.15 | 0.15 | 0.15 | 0.15 | 0.15 | 0.15 | 0.15 | 0.15 | 0.15 | 0.15 |
| Water | | | | | | to 100 | | | | | |

TABLE 2

O/W emulsions, numbers in % by weight

| | 2-1 | 2-2 | 2-3 | 2-4 | 2-5 | 2-6 | 2-7 | 2-8 | 2-9 | 2-10 |
|---|---|---|---|---|---|---|---|---|---|---|
| Titanium Dioxide | | 2 | 5 | | | | | | | 3 |
| Methylene Bis-Benzotriazolyl Tetramethylbutylphenol | | | | | | 1 | 2 | 1 | | |
| Phenethyl 3,4-Dihydroxyphenyl-propionate | | | | 1 | 2 | | | | 1 | 1 |
| 2-Ethylhexyl 4-Hydroxyphenyl-propionate | 1 | 3 | | 2 | | 5 | | 5 | 2 | |
| Di-2-ethylhexyl 4-Hydroxy-3,5-dimethoxybenzylmalonate | 5 | 5 | 5 | 5 | 5 | 5 | 5 | 5 | 5 | 5 |
| Di-2-ethylhexyl 2-Cyano-3,3-diphenylpropionate | 1 | 5 | 4 | | 6 | | 7 | | 2 | 1 |
| 4-Methylbenzylidene Camphor | 2 | | 3 | | 4 | | 3 | | 2 | |
| BMDBM | 1 | 3 | | 3 | 3 | | 3 | 3 | 3 | |
| Stearyl Alcohol (and) Steareth-7 (and) Steareth-10 | 3 | 3 | 3 | 3 | 3 | 3 | 3 | 3 | 3 | 3 |
| Glyceryl Stearate (and) Ceteth-20 | 3 | 3 | 3 | 3 | 3 | 3 | 3 | 3 | 3 | 3 |
| Glyceryl Stearate | 3 | 3 | 3 | 3 | 3 | 3 | 3 | 3 | 3 | 3 |
| Microwax | 1 | 1 | 1 | 1 | 1 | 1 | 1 | 1 | 1 | 1 |
| Cetearyl Octanoate | 11.5 | 11.5 | 11.5 | 11.5 | 11.5 | 11.5 | 11.5 | 11.5 | 11.5 | 11.5 |
| Caprylic/Capric Triglyceride | 6 | 6 | 6 | 6 | 6 | 6 | 6 | 6 | 6 | 6 |
| Oleyl Oleate | 6 | 6 | 6 | 6 | 6 | 6 | 6 | 6 | 6 | 6 |
| Propylene Glycol | 4 | 4 | 4 | 4 | 4 | 4 | 4 | 4 | 4 | 4 |
| Glyceryl Stearate SE | | | | | | | | | | |
| Stearic Acid | | | | | | | | | | |
| Persea Gratissima | | | | | | | | | | |
| Propylparaben | 0.05 | 0.05 | 0.05 | 0.05 | 0.05 | 0.05 | 0.05 | 0.05 | 0.05 | 0.05 |
| Methylparaben | 0.15 | 0.15 | 0.15 | 0.15 | 0.15 | 0.15 | 0.15 | 0.15 | 0.15 | 0.15 |
| Tromethamine | | | 1.8 | | | | | | | |
| Water | to 100 | to 100 | to 100 | to 100 | to 100 | to 100 | to 100 | to 100 | to 100 | to 100 |

| | 2-11 | 2-12 | 2-13 | 2-14 | 2-15 | 2-16 | 2-17 | 2-18 |
|---|---|---|---|---|---|---|---|---|
| Titanium Dioxide | 3 | | 2 | | | | 2 | 5 |
| Benzylidene Malonate Polysiloxane | | 1 | 0.5 | | | | | |
| Phenethyl 3,4-Dihydroxyphenyl-propionate | 1 | 1 | 0.5 | | | | | |
| Di-2-ethylhexyl 4-Hydroxy-3,5-dimethoxybenzylmalonate | | | | 1 | 2 | | | |
| Di-2-ethylhexyl 2-Cyano-3,3-diphenylpropionate | 1 | 3 | | 2 | | 5 | | 5 |
| 5,6,7-Trihydroxyflavone | 5 | 5 | 5 | 5 | 5 | 5 | 5 | 5 |
| 2-Ethylhexyl 4-Hydroxyphenyl-propionate | 1 | 5 | 4 | | 6 | | 7 | |
| Zinc Oxide | | | | 2 | | | | |
| UV-Pearl, OMC | 15 | 15 | 15 | 30 | 30 | 30 | 15 | 15 |
| 4-Methylbenzylidene Camphor | | | | 3 | | | | |
| BMDBM | | | | 1 | | | | |
| Phenylbenzimidazole Sulfonic Acid | | | | 4 | | | | |

TABLE 2-continued

O/W emulsions, numbers in % by weight

| | | | | | | | | |
|---|---|---|---|---|---|---|---|---|
| Stearyl Alcohol (and) Steareth-7 (and) Steareth-10 | 3 | 3 | 3 | 3 | | | | |
| Glyceryl Stearate (and) Ceteth-20 | 3 | 3 | 3 | 3 | | | | |
| Glyceryl Stearate | 3 | 3 | 3 | 3 | | | | |
| Microwax | 1 | 1 | 1 | 1 | | | | |
| Cetearyl Octanoate | 11.5 | 11.5 | 11.5 | 11.5 | | | | |
| Caprylic/Capric Triglyceride | 6 | 6 | 6 | 6 | 14 | 14 | 14 | 14 |
| Oleyl Oleate | 6 | 6 | 6 | 6 | | | | |
| Propylene Glycol | 4 | 4 | 4 | 4 | | | | |
| Glyceryl Stearate SE | | | | | 6 | 6 | 6 | 6 |
| Stearic Acid | | | | | 2 | 2 | 2 | 2 |
| Persea Gratissima | | | | | 8 | 8 | 8 | 8 |
| Propylparaben | 0.05 | 0.05 | 0.05 | 0.05 | 0.05 | 0.05 | 0.05 | 0.05 |
| Methylparaben | 0.15 | 0.15 | 0.15 | 0.15 | 0.15 | 0.15 | 0.15 | 0.15 |
| Tromethamine | | | | | 1.8 | | | |
| Glycerin | | | | | 3 | 3 | 3 | 3 |
| Water | to 100 | to 100 | to 100 | to 100 | to 100 | to 100 | to 100 | to 100 |

| | 2-19 | 2-20 | 2-21 | 2-22 | 2-23 | 2-24 | 2-25 | 2-26 | 2-27 | 2-28 |
|---|---|---|---|---|---|---|---|---|---|---|
| Titanium Dioxide | | | | | | | 3 | 3 | | 2 |
| Benzylidene Malonate Polysiloxane | 1 | 2 | | | | 1 | 1 | | 1 | 0.5 |
| 7,8,3',4'-Tetrahydroxyflavone | | | 1 | 2 | | | | | 1 | 1 |
| 2-Ethylhexyl 4-Hydroxyphenyl-propionate | 1 | 3 | | 2 | | 5 | | 5 | 2 | |
| Di-2-ethylhexyl 2-Cyano-3,3-diphenylpropionate | 5 | 5 | 5 | 5 | 5 | 5 | 5 | 5 | 5 | 5 |
| Di-2-ethylhexyl 4-Hydroxy-3,5-dimethoxybenzylmalonate | 1 | 5 | 4 | | 6 | | 7 | | 2 | 1 |
| Phenethyl 3,4-Dihydroxy-phenylpropionate | | | 1 | 2 | 1 | | | 1 | 1 | 0.5 |
| Zinc Oxide | | | | | 5 | 2 | | | | 2 |
| UV-Pearl, OMC | 15 | 15 | 15 | 15 | 15 | 15 | 15 | 15 | 15 | 15 |
| Caprylic/Capric Triglyceride | 14 | 14 | 14 | 14 | 14 | 14 | 14 | 14 | 14 | 14 |
| Oleyl Oleate | | | | | | | | | | |
| Propylene Glycol | | | | | | | | | | |
| Glyceryl Stearate SE | 6 | 6 | 6 | 6 | 6 | 6 | 6 | 6 | 6 | 6 |
| Stearic Acid | 2 | 2 | 2 | 2 | 2 | 2 | 2 | 2 | 2 | 2 |
| Persea Gratissima | 8 | 8 | 8 | 8 | 8 | 8 | 8 | 8 | 8 | 8 |
| Propylparaben | 0.05 | 0.05 | 0.05 | 0.05 | 0.05 | 0.05 | 0.05 | 0.05 | 0.05 | 0.05 |
| Methylparaben | 0.15 | 0.15 | 0.15 | 0.15 | 0.15 | 0.15 | 0.15 | 0.15 | 0.15 | 0.15 |
| Glyceryl Stearate, Ceteareth-20, Ceteareth-10, Cetearyl Alcohol, Cetyl Palmitate | | | | | | | | | | |
| Ceteareth-30 | | | | | | | | | | |
| Dicaprylyl Ether | | | | | | | | | | |
| Glycerin | 3 | 3 | 3 | 3 | 3 | 3 | 3 | 3 | 3 | 3 |
| Water | to 100 | to 100 | to 100 | to 100 | to 100 | to 100 | to 100 | to 100 | to 100 | to 100 |

TABLE 3

Gels, numbers in % by weight

| | 3-1 | 3-2 | 3-3 | 3-4 | 3-5 | 3-6 | 3-7 | 3-8 | 3-9 | 3-10 |
|---|---|---|---|---|---|---|---|---|---|---|
| A = aqueous gel | | | | | | | | | | |
| Titanium Dioxide | | 2 | 5 | | | | | | | 3 |
| 5,6,7-Trihydroxyflavone | | | | 1 | 2 | | | | 1 | 1 |
| Di-2-ethylhexyl 4-Hydroxy-3,5-dimethoxybenzylmalonate | 1 | 3 | | 2 | | 5 | | 5 | 2 | |
| Di-2-ethylhexyl 2-Cyano-3,3-diphenylpropionate | 5 | 5 | 5 | 5 | 5 | 5 | 5 | 5 | 5 | 5 |
| 2-Ethylhexyl 4-Hydroxyphenyl-propionate | 1 | 5 | 4 | | 6 | | 7 | | 2 | 1 |
| Benzylidene Malonate Polysiloxane | | | 1 | 1 | 2 | | | | 1 | 1 |
| Methylene Bis-Benzotriazolyl Tetramethylbutylphenol | | 1 | | | | 1 | 2 | 1 | | |
| Zinc Oxide | | | | 2 | | | | 5 | 2 | |
| UV-Pearl, Ethylhexyl Methoxycinnamate | 30 | 15 | 15 | 15 | 15 | 15 | 15 | 15 | 15 | 15 |
| 4-Methylbenzylidene Camphor | | | | | 2 | | | | | |
| Butylmethoxydibenzoylmethane | | 1 | | | | | | | | |
| Phenylbenzimidazole Sulfonic Acid | | | 4 | | | | | | | |
| Prunus Dulcis | 5 | 5 | 5 | 5 | 5 | 5 | 5 | 5 | 5 | 5 |

TABLE 3-continued

| Gels, numbers in % by weight | | | | | | | | | | |
|---|---|---|---|---|---|---|---|---|---|---|
| Tocopheryl Acetate | 0.5 | 0.5 | 0.5 | 0.5 | 0.5 | 0.5 | 0.5 | 0.5 | 0.5 | 0.5 |
| Caprylic/Capric Triglyceride | 3 | 3 | 3 | 3 | 3 | 3 | 3 | 3 | 3 | 3 |
| Octyldodecanol | 2 | 2 | 2 | 2 | 2 | 2 | 2 | 2 | 2 | 2 |
| Decyl Oleate | 2 | 2 | 2 | 2 | 2 | 2 | 2 | 2 | 2 | 2 |
| PEG-8 (and) Tocopherol (and) Ascorbyl Palmitate (and) Ascorbic Acid (and) Citric Acid | 0.05 | 0.05 | 0.05 | 0.05 | 0.05 | 0.05 | 0.05 | 0.05 | 0.05 | 0.05 |
| Sorbitol | 4 | 4 | 4 | 4 | 4 | 4 | 4 | 4 | 4 | 4 |
| Polyacrylamide (and) C13-14 Isoparaffin (and) Laureth-7 | 3 | 3 | 3 | 3 | 3 | 3 | 3 | 3 | 3 | 3 |
| Propylparaben | 0.05 | 0.05 | 0.05 | 0.05 | 0.05 | 0.05 | 0.05 | 0.05 | 0.05 | 0.05 |
| Methylparaben | 0.15 | 0.15 | 0.15 | 0.15 | 0.15 | 0.15 | 0.15 | 0.15 | 0.15 | 0.15 |
| Tromethamine | | | 1.8 | | | | | | | |
| Water | to 100 | to 100 | to 100 | to 100 | to 100 | to 100 | to 100 | to 100 | to 100 | to 100 |

| | 3-11 | 3-12 | 3-13 | 3-14 | 3-15 | 3-16 | 3-17 | 3-18 |
|---|---|---|---|---|---|---|---|---|
| a = aqueous gel | | | | a | a | a | a | a |
| Titanium Dioxide | 3 | | 2 | | | | | |
| Benzylidene Malonate Polysiloxane | | 1 | 0.5 | 1 | 2 | | | |
| Methylene Bis-Benzotriazolyl Tetramethylbutylphenol | 1 | 1 | 0.5 | | | 1 | 2 | 1 |
| Di-2-ethylhexyl 4-Hydroxy-3,5-dimethoxybenzylmalonate | | | | 1 | 2 | | | |
| 2-Ethylhexyl 4-Hydroxyphenylpropionate | 1 | 3 | | 2 | | 5 | | 5 |
| Di-2-ethylhexyl 2-Cyano-3,3-diphenyl-propionate | 5 | 5 | 5 | 5 | 5 | 5 | 5 | 5 |
| 6,3',4'-Trihydroxyflavone | 1 | 5 | 4 | | 6 | | 7 | |
| Zinc Oxide | | | 2 | | | | | |
| UV-Pearl, Ethylhexyl Methoxycinnamate | 15 | 15 | 15 | 15 | 15 | 15 | 15 | 15 |
| Prunus Dulcis | 5 | 5 | 5 | | | | | |
| Tocopheryl Acetate | 0.5 | 0.5 | 0.5 | | | | | |
| Caprylic/Capric Triglyceride | 3 | 3 | 3 | | | | | |
| Octyldodecanol | 2 | 2 | 2 | | | | | |
| Decyl Oleate | 2 | 2 | 2 | | | | | |
| PEG-8 (and) Tocopherol (and) Ascorbyl Palmitate (and) Ascorbic Acid (and) Citric Acid | 0.05 | 0.05 | 0.05 | | | | | |
| Sorbitol | 4 | 4 | 4 | 5 | 5 | 5 | 5 | 5 |
| Polyacrylamide (and) C13-14 Isoparaffin (and) Laureth-7 | 3 | 3 | 3 | | | | | |
| Carbomer | | | | 1.5 | 1.5 | 1.5 | 1.5 | 1.5 |
| Propylparaben | 0.05 | 0.05 | 0.05 | | | | | |
| Methylparaben | 0.15 | 0.15 | 0.15 | 0.15 | 0.15 | 0.15 | 0.15 | 0.15 |
| Allantoin | | | | 0.2 | 0.2 | 0.2 | 0.2 | 0.2 |
| Tromethamine | | | | 2.4 | 2.4 | 2.4 | 2.4 | 2.4 |
| Water | to 100 | to 100 | to 100 | to 100 | to 100 | to 100 | to 100 | to 100 |

| | 3-19 | 3-20 | 3-21 | 3-22 | 3-23 | 3-24 | 3-25 | 3-26 | 3-27 | 3-28 |
|---|---|---|---|---|---|---|---|---|---|---|
| 7,8,3',4'-Tetrahydroxyflavone | | | | 1 | 2 | | | | 1 | 1 |
| Di-2-ethylhexyl 4-Hydroxy-3,5-dimethoxybenzylmalonate | 1 | 3 | | 2 | | 5 | | 5 | 2 | |
| Di-2-ethylhexyl 2-Cyano-3,3-diphenylpropionate | 5 | 5 | 5 | 5 | 5 | 5 | 5 | 5 | 5 | 5 |
| 2-Ethylhexyl 4-Hydroxyphenyl-propionate | 1 | 5 | 4 | | 6 | | 7 | | 2 | 1 |
| UV-Pearl, OMC | 30 | 30 | 15 | 15 | 15 | 11 | 12 | 15 | 15 | 15 |
| Phenylbenzimidazole Sulfonic Acid | | 4 | 4 | | | | | | | |
| Sorbitol | 5 | 5 | 5 | 5 | 5 | 5 | 5 | 5 | 5 | 5 |
| Carbomer | 1.5 | 1.5 | 1.5 | 1.5 | 1.5 | 1.5 | 1.5 | 1.5 | 1.5 | 1.5 |
| Propylparaben | | | | | | | | | | |
| Methylparaben | 0.15 | 0.15 | 0.15 | 0.15 | 0.15 | 0.15 | 0.15 | 0.15 | 0.15 | 0.15 |
| Allantoin | 0.2 | 0.2 | 0.2 | 0.2 | 0.2 | 0.2 | 0.2 | 0.2 | 0.2 | 0.2 |
| Tromethamine | 2.4 | 4.2 | 4.2 | 2.4 | 2.4 | 2.4 | 2.4 | 2.4 | 2.4 | 2.4 |
| Water | to 100 | to 100 | to 100 | to 100 | to 100 | to 100 | to 100 | to 100 | to 100 | to 100 |

| | 3-29 | 3-30 | 3-31 | 3-32 | 3-33 | 3-34 | 3-35 | 3-36 |
|---|---|---|---|---|---|---|---|---|
| 2-Ethylhexyl 4-Hydroxyphenylpropionate | | | | 1 | 2 | | | |
| Di-2-ethylhexyl 2-Cyano-3,3-diphenylpropionate | 1 | 3 | | 2 | | 5 | | 5 |
| Di-2-ethylhexyl 4-Hydroxy-3,5-dimethoxybenzyl-malonate | 5 | 5 | 5 | 5 | 5 | 5 | 5 | 5 |
| 5,6,7-Trihydroxyflavone | 1 | 5 | 4 | | 6 | | 7 | |
| UV-Pearl, OMC | | 15 | 10 | | 10 | 10 | 15 | 10 |

TABLE 3-continued

| | Gels, numbers in % by weight | | | | | | | |
|---|---|---|---|---|---|---|---|---|
| UV-Pearl, OCR | | | 10 | | | | | |
| UV-Pearl, OMC, Methylene Bis-Benzotriazolyl Tetramethylbutylphenol | | 7 | | 6 | | | | |
| UV-Pearl, Ethylhexyl Salicylate, BMDBM | | | 10 | | | | | |
| Disodium Phenyl Dibenzimidazole Tetrasulfonate | | 3 | | | | 3 | | 3 |
| Phenylbenzimidazole Sulfonic Acid | | 2 | | | 2 | 3 | | 3 |
| Prunus Dulcis | 5 | 5 | 5 | | | | | |
| Tocopheryl Acetate | 0.5 | 0.5 | 0.5 | | | | | |
| Caprylic/Capric Triglyceride | 3 | 3 | 3 | | | | | |
| Octyldodecanol | 2 | 2 | 2 | | | | | |
| Decyl Oleate | 2 | 2 | 2 | | | | | |
| PEG-8 (and) Tocopherol (and) Ascorbyl Palmitate (and) Ascorbic Acid (and) Citric Acid | 0.05 | 0.05 | 0.05 | | | | | |
| Sorbitol | 4 | 4 | 4 | 5 | 5 | 5 | 5 | 5 |
| Polyacrylamide (and) C13-14 Isoparaffin (and) Laureth-7 | 3 | 3 | 3 | | | | | |
| Carbomer | | | | 1.5 | 1.5 | 1.5 | 1.5 | 1.5 |
| Propylparaben | 0.05 | 0.05 | 0.05 | | | | | |
| Methylparaben | 0.15 | 0.15 | 0.15 | 0.15 | 0.15 | 0.15 | 0.15 | 0.15 |
| Allantoin | | | | 0.2 | 0.2 | 0.2 | 0.2 | 0.2 |
| Tromethamine | | | | 2.4 | 2.4 | 2.4 | 2.4 | 2.4 |
| Water | to 100 | to 100 | to 100 | to 100 | to 100 | to 100 | to 100 | to 100 |

Example 5

Hair Mascara

| Ingredients | [%] |
|---|---|
| A | |
| PEARLESCENT PIGMENT | 20.00 |
| B | |
| CETEARETH-25 | 1.80 |
| CETEARYL ALCOHOL | 5.00 |
| DIMETHICONE | 1.00 |
| PHENOXYETHANOL, BUTYLPARABEN, ETHYLPARABEN, PROPYLPARABEN, METHYLPARABEN | 0.50 |
| C | |
| AQUA (WATER) | to 100 |
| POLYQUATERNIUM-16 | 3.0 |
| PROPYLENE GLYCOL | 1.80 |
| COMPOUND OF FORMULA IB-IAH | 0.5 |
| D | |
| AQUA (WATER) | 9.50 |
| HYDROXYPROPYLCELLULOSE | 0.50 |
| E | |
| AQUA (WATER) | 9.50 |
| MAGNESIUM ALUMINIUM SILICATE | 0.50 |
| IMIDAZOLIDINYL UREA | 0.30 |

Preparation Process:

Heat phase B to 75° C., phase C to 80° C. Slowly add phase B to phase C with stirring. Cool to 65° C. with stirring, and homogenise. Cool to 40° C., and add phases D, E and F to phase B/C with stirring, and again homogenise. Now add the pearlescent pigment with stirring. Cool to room temperature, and adjust the pH to 6.0-6.5.

Hair mascara compositions which have the following modifications can be prepared analogously:

| POLYQUATERNIUM-16 | 0 |
|---|---|
| COMPOUND OF FORMULA IB-IAH | 4.0 |

| POLYQUATERNIUM-16 | 0.5 |
|---|---|
| COMPOUND OF FORMULA IB-IAH | 3.0 |

| POLYQUATERNIUM-16 | 1 |
|---|---|
| COMPOUND OF FORMULA IB-IAH | 3 |

| POLYQUATERNIUM-16 | 1 |
|---|---|
| COMPOUND OF FORMULA IB-IAH | 3.5 |

| POLYQUATERNIUM-16 | 2 |
|---|---|
| COMPOUND OF FORMULA IB-IAH | 2 |

| POLYQUATERNIUM-16 | 1.5 |
|---|---|
| COMPOUND OF FORMULA IB-IAH | 1 |

| POLYQUATERNIUM-16 | 2.5 |
|---|---|
| COMPOUND OF FORMULA IB-IAH | 1.5 |

| | |
|---|---|
| POLYQUATERNIUM-16 | 1 |
| COMPOUND OF FORMULA IB-IAH | 2.5 |

Example 6

Conditioner Comprising IR3535®

| Ingredients | [%] |
|---|---|
| A | |
| ETHYLBUTYL ACETYLAMINOPROPIONATE | 10.00 |
| PVP/VA COPOLYMER | 4.00 |
| PERFUME | 0.30 |
| QUATERNIUM-80 | 1.0 |
| PEG-40 HYDROGENATED CASTOR OIL | 1.00 |
| ALCOHOL | 15.00 |
| COMPOUND OF FORMULA IB-IAH | 2.0% |
| B | |
| CETRIMONIUM CHLORIDE | 0.50 |
| AQUA (WATER) | To 100 |
| C | |
| COCAMIDOPROPYL BETAINE | 4.00 |

Preparation process: Mix phases A and B separately. Add phase B to phase A with stirring. Add phase C.

Conditioner compositions which have the following modifications can be prepared analogously:

| | |
|---|---|
| QUATERNIUM-80 | 2.0 |
| COMPOUND OF FORMULA IB-IAH | 1.0 |

| | |
|---|---|
| QUATERNIUM-80 | 0 |
| COMPOUND OF FORMULA IB-IAH | 3.0 |

| | |
|---|---|
| QUATERNIUM-80 | 1.0 |
| COMPOUND OF FORMULA IB-IAH | 2.5 |

| | |
|---|---|
| QUATERNIUM-80 | 2.0 |
| COMPOUND OF FORMULA IB-IAH | 1.5 |

| | |
|---|---|
| QUATERNIUM-80 | 2.0 |
| COMPOUND OF FORMULA IB-IAH | 3.0 |

| | |
|---|---|
| QUATERNIUM-80 | 0.5 |
| COMPOUND OF FORMULA IB-IAH | 2.5 |

| | |
|---|---|
| QUATERNIUM-80 | 1.0 |
| COMPOUND OF FORMULA IB-IAH | 3.0 |

| | |
|---|---|
| QUATERNIUM-80 | 2.5 |
| COMPOUND OF FORMULA IB-IAH | 1.5 |

| | |
|---|---|
| QUATERNIUM-80 | 1.8 |
| COMPOUND OF FORMULA IB-IAH | 2.1 |

Example 7

Hair Conditioner Comprising Pearlescent Pigment

| Ingredients | [%] |
|---|---|
| A | |
| PEARLESCENT PIGMENT | 3.00 |
| DISODIUM EDTA | 0.05 |
| AQUA (WATER) | to 100 |
| B | |
| CETEARYL ALCOHOL, BEHENTRIMONIUM METHOSULFATE | 5.00 |
| OCTYLDODECANOL | 1.10 |
| CETYL ALCOHOL | 1.00 |
| GLYCERIN | 1.00 |
| BEHENTRIMONIUM CHLORIDE | 0.70 |
| METHOXY PEG/PPG-7/3 AMINOPROPYL DIMETHICONE | 0.70 |
| QUATERNIUM-80 | 1.0 |
| COMPOUND OF FORMULA IB-IAH | 2.0 |
| C | |
| COCODIMONIUM HYDROXYPROPYLSILICAMINO ACIDS | 0.70 |
| PHENOXYETHANOL, BENZOIC ACID, DEHYDROACETIC ACID | 0.40 |
| CITRIC ACID | 0.20 |
| PERFUME | 0.60 |

Preparation Process:

Disperse the pearlescent pigment and Titriplex III in the water of phase A. Heat the constituents of phases A and B to 75° C. Add phase B to phase A with stirring, and homogenise. Cool to 40° C., and add the constituents of phase C. Cool to 30° C., and again homogenise for about 30 sec. Adjust the pH to 3.6-4.0.

Notes: recommended pearlescent pigments are TIMIRON® silver pigments and TIMIRON® interference pigments from Merck.

Conditioner compositions which have the following modifications can be prepared analogously to Example 7:

| QUATERNIUM-80 | 2.0 |
| --- | --- |
| COMPOUND OF FORMULA IB-IAH | 1.0 |

| QUATERNIUM-80 | 0 |
| --- | --- |
| COMPOUND OF FORMULA IB-IAH | 3.0 |

| QUATERNIUM-80 | 1.0 |
| --- | --- |
| COMPOUND OF FORMULA IB-IAH | 2.5 |

| QUATERNIUM-80 | 2.0 |
| --- | --- |
| COMPOUND OF FORMULA IB-IAH | 1.5 |

| QUATERNIUM-80 | 2.0 |
| --- | --- |
| COMPOUND OF FORMULA IB-IAH | 3.0 |

| QUATERNIUM-80 | 0.5 |
| --- | --- |
| COMPOUND OF FORMULA IB-IAH | 2.5 |

| QUATERNIUM-80 | 1.0 |
| --- | --- |
| COMPOUND OF FORMULA IB-IAH | 3.0 |

| QUATERNIUM-80 | 2.5 |
| --- | --- |
| COMPOUND OF FORMULA IB-IAH | 1.5 |

| QUATERNIUM-80 | 1.8 |
| --- | --- |
| COMPOUND OF FORMULA IB-IAH | 2.1 |

INDEX OF THE FIGURES

Figure 1B:
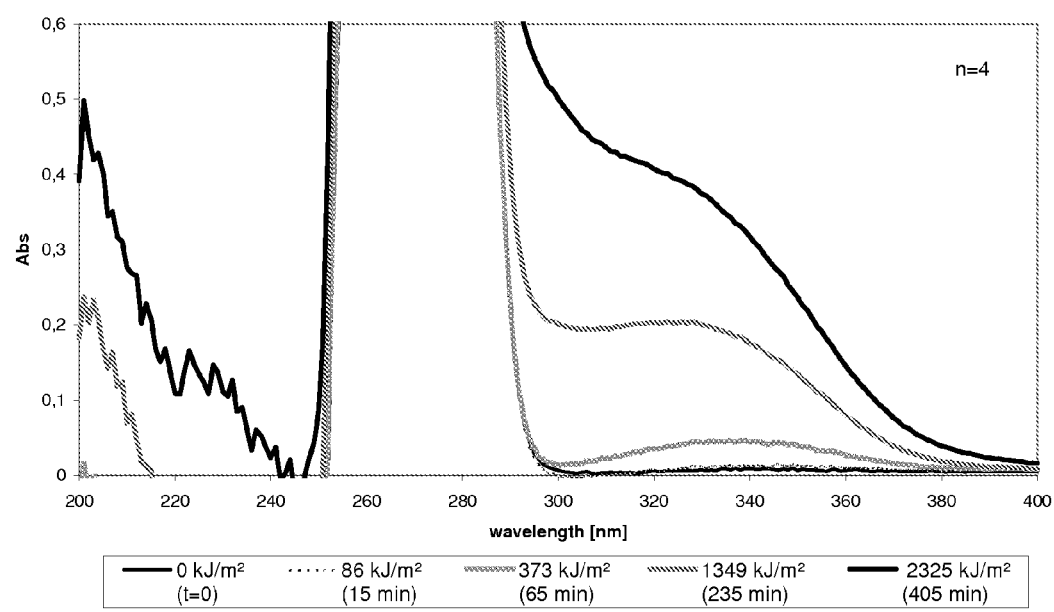

FIGS. 1a and 1b:

FIG. 1 (FIG. 1b represents a detail of FIG. 1a) shows the change in the UV spectrum of di-2-ethylhexyl 4-hydroxy-3,5-dimethoxybenzylmalonate on irradiation with UV light (cf. Example 3): the curves stand for the unirradiated substance (exposed to 0 kJ/m$^2$), after irradiation for 15 min (exposure to 86 kJ/m$^2$), after irradiation for 65 min (exposure to 373 kJ/m$^2$), after irradiation for 235 min (exposure to 1349 kJ/m$^2$) and after irradiation for 405 min (exposure to 2325 kJ/m$^2$). The spectra are recorded on a Carry 300 bio spectrometer. The irradiation is carried out by means of an Atlas Sun Test CPS, xenon lamp with UV special-glass filter at a power of 95.69 W/m$^2$ in the range 290-400 nm. The results are from 4-fold determinations (n=4).

FIG. 2:

FIG. 2 shows the change in the UV/VIS spectrum of emulsions comprising 0.5% by weight of beta-carotene and 4% by weight of di-2-ethylhexyl 4-hydroxy-3,5-dimethoxybenzylmalonate (curves A and B) compared with an emulsion comprising 0.5% by weight of beta-carotene, but no di-2-ethylhexyl 4-hydroxy-3,5-dimethoxybenzylmalonate (curves C and D) on irradiation with UV light (cf. Example 3a): the curves stand for the unirradiated emulsions (curves A and C) and the emulsions after irradiation for 90 min (curves B and D). The spectra are recorded on a Carry 300 bio spectrometer. The irradiation is carried out by means of an Atlas Sun Test CPS, xenon lamp with UV special-glass filter at a power of 95.69 W/m$^2$ in the range 290-400 nm. The results are from 4-fold determinations (n=4).

The invention claimed is:

1. A method of achieving UV-A or UV-B protection comprising employing compounds which do not themselves exhibit significant UV absorption in the UV-A or UV-B region, but are reactive under use conditions, for the development of UV-A or UV-B protection during use wherein said compounds are compounds of the formula I

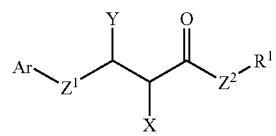

where

Ar stands for an unsubstituted or mono- or polysubstituted aromatic ring or condensed ring systems having 6 to 18 C atoms, at least one ring of which has an aromatic character and in which one or two CH groups per ring may be replaced by C=O, N, O or S and, in addition, one or two CH$_2$ groups in a condensed ring system may be replaced by C=O or C=CH$_2$, R$^1$ stands for H or a branched or unbranched C$_{1-30}$-alkyl or C$_{1-30}$-hydroxyalkyl radical or a radical R$^a$ or R$^b$

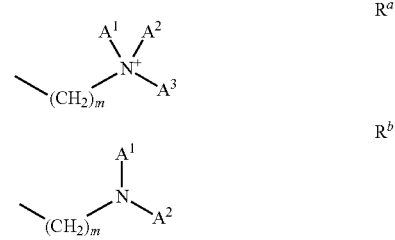

where m stands for an integer from the range from 1 to 30, and A$^1$-A$^3$ each, independently of one another, stand for a benzyl radical or a —(CH$_2$O)$_n$(CH$_2$)$_o$(O)$_p$H radical, where m and o each, independently of one another, stand for an integer from the range from 0 to 30, and p stands for 0 or 1, X stands for a group selected from —H, —CN, —C(=O)—R$^1$ and —C(=O)—Z$^2$—R$^1$, Y stands for H or Ar, Z$^1$ and Z$^2$ each, independently of one another, stand for O, S, CR$^7$R$^8$, NR$^7$ or a single bond, R$^7$ and R$^8$ are each, independently of one another, selected from H, OH, straight-chain or branched C$_1$- to C$_{20}$-alkoxy groups, straight-chain or branched C$_1$- to C$_{20}$-alkyl groups, straight-chain or branched C$_3$- to C$_{20}$-alkenyl groups, straight-chain or branched C$_1$- to C$_{20}$-hydroxyalkyl groups, where the hydroxyl group may be bonded to a primary or secondary carbon atom of the chain and furthermore the alkyl chain may also be interrupted by oxygen, straight-chain or branched C$_1$- to C$_{20}$-hydroxyalkoxy groups, where the hydroxyl group(s) may be bonded to a primary or secondary carbon atom of the chain and furthermore the alkyl chain may also be interrupted by oxygen, or salts of the compounds of the formula I.

2. A method according to claim 1, wherein the compounds of the formula I are compounds of the formula Ia

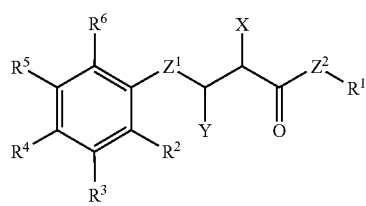

where

R$^1$, R$^7$ and R$^8$, Z$^1$ and Z$^2$, X and Y have the meaning given in claim 1, R$^2$ to R$^6$ are each, independently of one another, selected from H, OH, straight-chain or branched C$_1$- to C$_{20}$-alkoxy groups, straight-chain or branched C$_1$- to C$_{20}$-alkyl groups, straight-chain or branched C$_3$- to C$_{20}$-alkenyl groups, straight-chain or branched C$_1$- to C$_{20}$-hydroxyalkyl groups, where the hydroxyl group may be bonded to a primary or secondary carbon atom of the chain and furthermore the alkyl chain may also be interrupted by oxygen, straight-chain or branched C$_1$- to C$_{20}$-hydroxyalkoxy groups, where the hydroxyl group(s) may be bonded to a primary or secondary carbon atom of the chain and furthermore the alkyl chain may also be interrupted by oxygen, where one of the radicals R$^2$ to R$^6$ may also stand for a branched or unbranched C$_{1-20}$-alkoxy or branched or unbranched C$_{2-20}$-alkyleneoxy spacer which is bonded to an oligo- or polysiloxane chain via an Si atom, or salts of the compounds of the formula Ia.

3. A method according to claim 1, wherein the compound is used as UV filter precursor which can be activated by UV radiation.

4. A method according to claim 1, for the preparation of cosmetic or dermatological compositions or of foods or food supplements or for the preparation of domestic products.

5. A method according to claim 2, wherein R$^3$ and R$^5$ are each, independently of one another, selected from H, straight-chain or branched C$_1$- to C$_{20}$-alkoxy groups, straight-chain or branched C$_1$- to C$_{20}$-alkyl groups, straight-chain or branched C$_3$- to C$_{20}$-alkenyl groups, straight-chain or branched C$_1$- to C$_{20}$-hydroxyalkyl groups, where the hydroxyl group may be bonded to a primary or secondary carbon atom of the chain and furthermore the alkyl chain may also be interrupted by oxygen, straight-chain or branched C$_1$- to C$_{20}$-hydroxyalkoxy groups, where the hydroxyl group(s) may be bonded to a primary or secondary carbon atom of the chain and furthermore the alkyl chain may also be interrupted by oxygen, where R$^3$ and R$^5$ are each, independently of one another, R$^2$, R$^4$ and R$^6$ are each, independently of one another, selected from H, OH, straight-chain or branched C$_1$- to C$_{20}$-alkoxy groups, straight-chain or branched C$_1$- to C$_{20}$-alkyl groups, straight-chain or branched C$_3$- to C$_{20}$-alkenyl groups, straight-chain or branched C$_1$- to C$_{20}$-hydroxyalkyl groups, where the hydroxyl group may be bonded to a primary or secondary carbon atom of the chain and furthermore the alkyl chain may also be interrupted by oxygen, straight-chain or branched C$_1$- to C$_{20}$-hydroxyalkoxy groups, where the hydroxyl group(s) may be bonded to a primary or secondary carbon atom of the chain and furthermore the alkyl chain may also be interrupted by oxygen, and where one of the radicals R$^2$ to R$^6$ may also stand for a branched or unbranched C$_{1-20}$-alkoxy or branched or unbranched C$_{2-20}$-alkyleneoxy spacer which is bonded via an Si atom to an oligo- or polysiloxane chain, which in turn contains one or more compounds of the formula I.

6. A method according to claim 2, wherein at least one group from R$^2$, R$^4$ and R$^6$ stands for OH.

7. A method according to claim 2, wherein Z$^2$ stands for a single bond.

8. A method according to claim 1, wherein R$^1$ stands for a branched or unbranched C$_{7-30}$-alkyl or C$_{6-30}$-hydroxyalkyl radical.

9. A method according to claim 2, wherein R$^4$ stands for a branched or unbranched C$_{1-20}$-alkoxy or branched or unbranched C$_{2-20}$-alkylene-oxy spacer which is bonded via an Si atom to an oligo- or polysiloxane chain which contains one or more compounds of the formula I.

10. A method according to claim 1, wherein when X stands for —C(=O)—Z$^2$—R$^1$, then all radicals Z$^2$ in formula I are identical and all radicals R$^1$ in formula I are identical and R$^2$ to R$^6$ each, independently of one another, stand for H, hydroxyl or methoxy.

11. A method according to claim 1, wherein the at least one compound is selected from 4-hydroxyphenylpropionic acid, 2-ethylhexyl 4-hydroxyphenylpropionate, di-2-ethylhexyl 4-hydroxy-3,5-dimethoxy-benzylmalonate, di-2-ethylhexyl 4-methoxybenzylmalonate, 2-ethylhexyl 4-methoxyphenylpropionate, 2-ethylhexyl 4-hydroxy-3,5-dimethoxyphenylpropionate, di-2-ethylhexyl 3,4,5-trimethoxybenzylmalonate, 2-ethylhexyl 4-hydroxy-3-methoxyphenylpropionate, di-2-ethylhexyl 4-hydroxy-3-methoxy-benzylmalonate, di-2-ethylhexyl 3,4-dihydroxybenzylmalonate, 2-ethylhexyl 3,4-dihydroxyphenylpropionate, 3,4-dihydroxyphenylpropionic acid, phenethyl 3,4-dihydroxyphenylpropionate, 2-ethylhexyl 2-cyano-3,3-diphenylpropionate and oligo- and polysiloxanes which contain benzylmalonic acid derivatives or phenylpropionic acid derivatives, diethyl p-benzylmalonate, bonded via propanyloxy, isopropanyloxy, propenyloxy, isopropenyloxy or allyloxy spacers.

12. A method according to claim 1, wherein $Z^1$ stands for NH, and $R^1$ stands for a radical $R^a$ or $R^b$

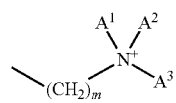
$R^a$

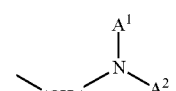
$R^b$ where m stands for an integer from the range from 1 to 3, and $A^1$-$A^3$ each, independently of one another, stand for H or a radical —$(CH_2)_o(O)_pH$, where o stands for 1, 2 or 3, and p stands for 0 or 1.

13. A method according to claim 12, wherein that the compound is selected from compounds Ib to Iah and salts thereof, in particular chlorides thereof,

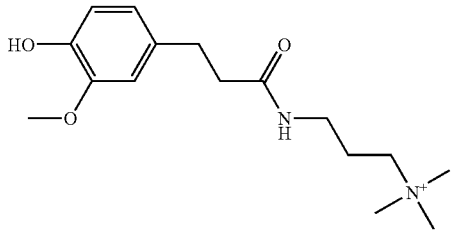
Iah

Ib

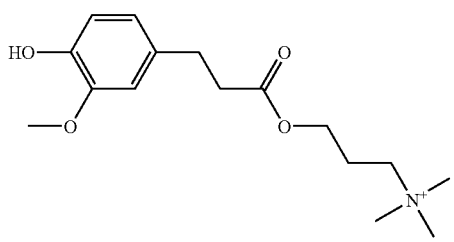
Ic

Id

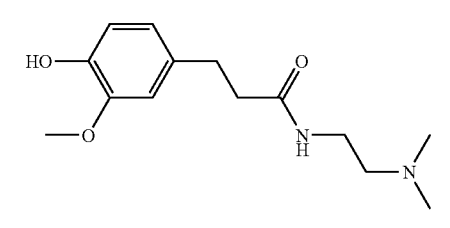
-continued

Ie

If

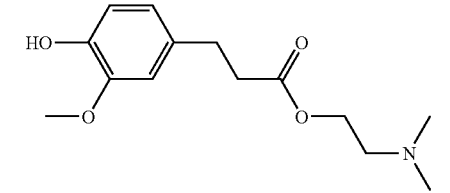
Ig

Ih

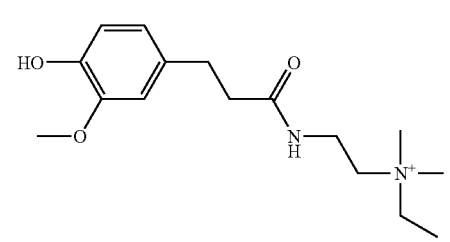
Ij

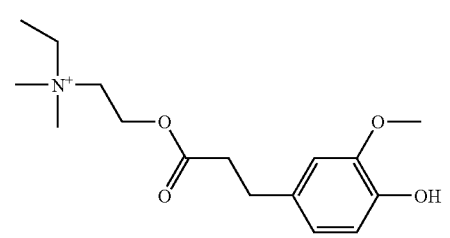
Ik

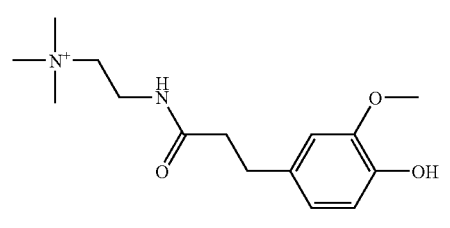
Im

-continued
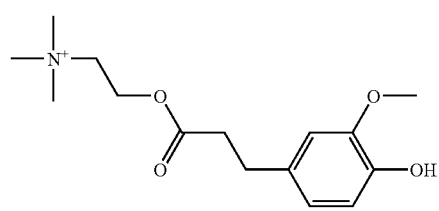
In
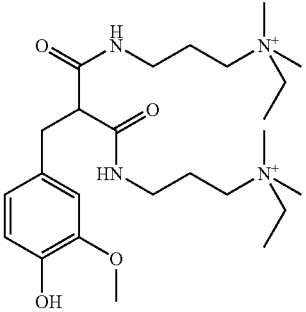
Io
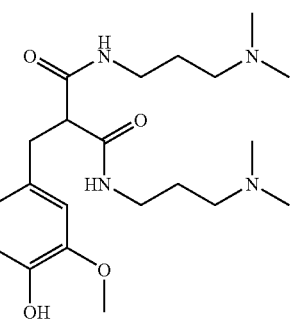
Ip
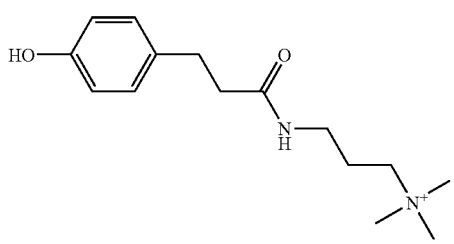
Iq
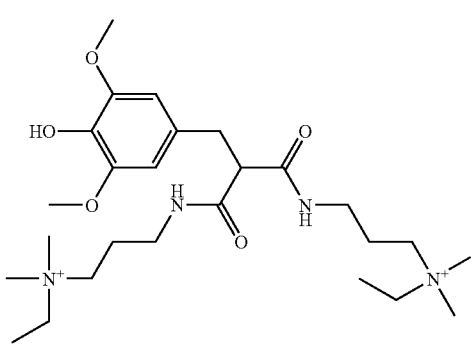
Ir
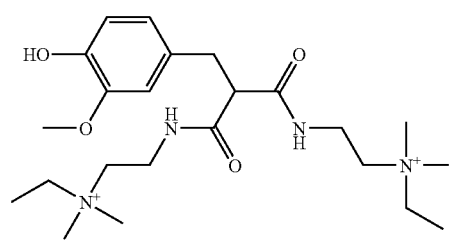
Is
-continued
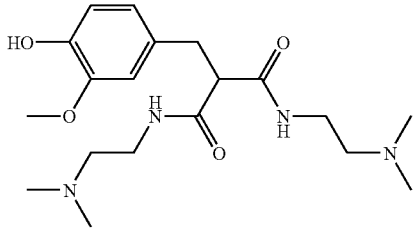
It
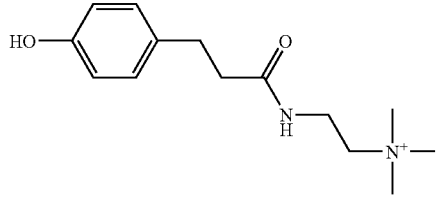
Iu
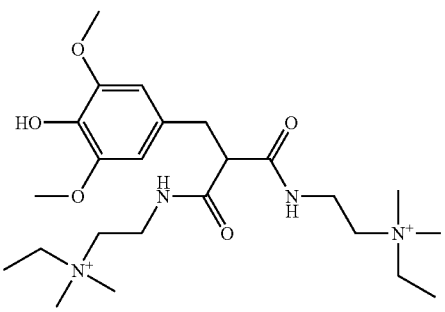
Iv
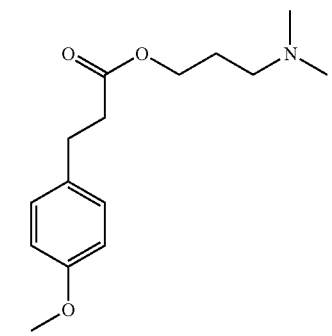
Iw
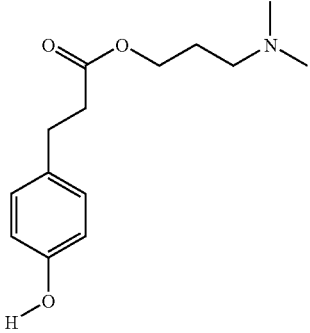
Ix -continued Iy
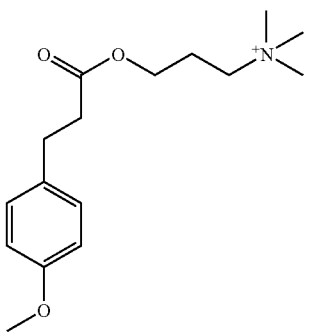

Iz
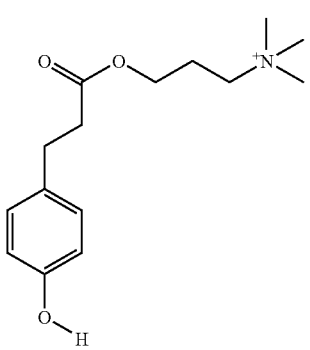

Iaa
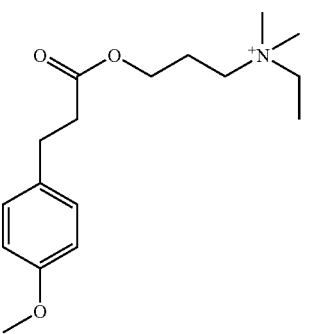

Iab
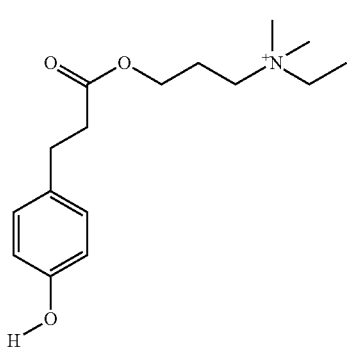

-continued

Iac
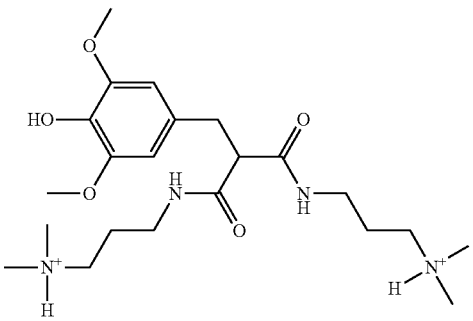

Iad
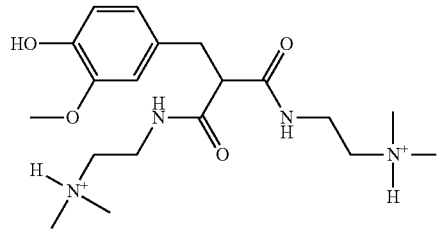

Iae
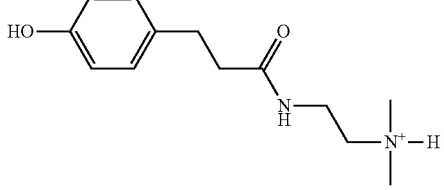

Iaf
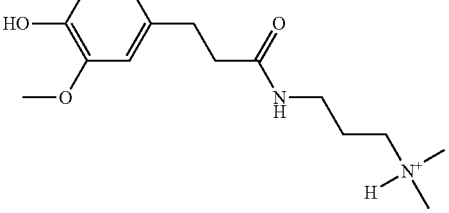

Iag
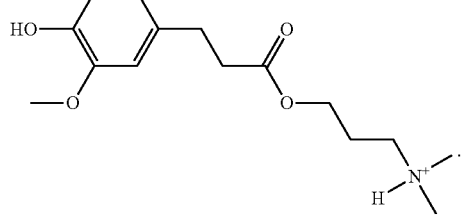

14. A method of claim 9, wherein $R^4$ stands for a propanyloxy, isopropanyloxy, propenyloxy, isopropenyloxy or an allyloxy spacer and where a silicon atom is bonded to the 1-C or 2-C of the spacer double bond.

15. A method according to claim 5, wherein where $R^3$ and $R^5$ are each, independently of one another, methoxy, isopropoxy, tert-butoxy, methyl, isopropyl or tert-butyl, and where $R^2$, $R^4$ and $R^6$ are each independently of each other H or OH.

\* \* \* \* \*